United States Patent
Giuliano et al.

(10) Patent No.: US 12,005,056 B2
(45) Date of Patent: Jun. 11, 2024

(54) CENTRALLY-ACTIVE GHRELIN AGONIST AND MEDICAL USES THEREOF

(71) Applicant: Helsinn Healthcare SA, Lugano-Pazzallo (CH)

(72) Inventors: Claudio Giuliano, Como (IT); Claudio Pietra, Como (IT); Silvina Garcia Rubio, Princeton, NJ (US); Angelo Guainazzi, New York, NY (US); Marielle Martinez-Loi, Biasca (CH)

(73) Assignee: Helsinn Healthcare SA, Pazzallo-Lugano (CH)

( * ) Notice: Subject to any disclaimer, the term of this patent is extended or adjusted under 35 U.S.C. 154(b) by 151 days.

(21) Appl. No.: 16/982,107

(22) PCT Filed: Mar. 14, 2019

(86) PCT No.: PCT/EP2019/056438
§ 371 (c)(1),
(2) Date: Sep. 18, 2020

(87) PCT Pub. No.: WO2019/179878
PCT Pub. Date: Sep. 26, 2019

(65) Prior Publication Data
US 2023/0158007 A1    May 25, 2023

(30) Foreign Application Priority Data
Mar. 22, 2018   (EP) .................... 18163425

(51) Int. Cl.
*A61K 31/4468* (2006.01)
(52) U.S. Cl.
CPC ................. *A61K 31/4468* (2013.01)
(58) Field of Classification Search
CPC .................................. A61K 31/4468
See application file for complete search history.

(56) References Cited

U.S. PATENT DOCUMENTS 8,658,797 B2 *  2/2014  Garcia Rubio ...... C07D 211/58
546/224

FOREIGN PATENT DOCUMENTS

WO          2012116176 A2     8/2012

OTHER PUBLICATIONS

Camargo-Silva et al. Life Sciences, 2018, vol. 196, p. 84-92 (Year: 2018).*
Gould (International Journal of Pharmaceutics, 1986, vol. 33, p. 201-217) (Year: 1986).*
Chiorazzi et al., "Effect of Preventative and Therapeutic Treatment of Ghrelin Agonist HM01 on the Peripheral Neurotoxicity Induced by Bortezomib in Wistar Rats," Journal of the Peripheral Nervous System, 22 Suppl 1:S10-11 (2017).
Karasawa et al., "New ghrelin agonist, HM01 alleviates constipation and L-dopa-delayed gastric emptying in 6-hydroxydopamine rat model of Parkinson's disease," Neurogastroenterolgy & Motility, 26(12):1771-1782 (2014).
Karasawa et al., "New ghrelin agonist, HM01 alleviates constipation and L-dopa-delayed gastric emptying in 6-hydroxydopamine rat model of Parkinson's disease," Neurogastroenterolgy & Motility, 26(12):1771-1782 (2014), HHS Public Access version, 24 pages.
Garcia et al., "Ghrelin prevents cisplatin-induced mechanical hyperalgesia and cachexia," Endocrinology, vol. 149, No. 2, pp. 455-462 (Feb. 2008).
International Search Report and Written Opinion of International Application No. PCT/EP2019/056438, dated Jul. 22, 2019 (10 pages).
Kamei et al., Rikkunshito prevents paclitaxel-induced peripheral neuropathy through the suppression of the nuclear factor kappa B (NF[kappa]B) phosphorylation in spinal cord of mice, PLOS One, vol. 12, No. 2, pp. E0171819-1 (Feb. 9, 2017).
Naitou et al., "Site and mechanism of the colokinetic action of the ghrelin receptor agonist, HOM1," Neurogastroenterology and Motility, vol. 27, No. 12, pp. 1764-1774 (Sep. 28, 2015).
Rudd et al., "Anti-emetic Action of the Brain-Penetrating New Ghrelin Agonist, HM01, Alone and in Combination With the 5-HT3 Antagonist, Palonosetron and With the NK1 Antagonist, Netupitant, Against Cisplatin- and Motion-Induced Emsis in *Suncus murinus* (House Musk Shrew)," Frontiers in Pharmacology, vol. 9 pp. 869-1 (Aug. 6, 2018).
Chiorazzi et al., "Effect of Preventative and Therapeutic Treatment of Ghrelin Agonist HM01 on the Peripheral Neurotoxicity Induced by Bortezomib in Wistar Rats," Journal of the Peripheral Nervous System, 22 Suppl 1:S10-11 2017 (42 pages).
Gahete et al., Role of ghrelin system in neuroprotection and cognitive functions: Implications in Alzheimer's disease, Peptides 32 (2011) pp. 2225-2228 (4 pages).
Jiang Jinghua, "Fundamentals of Medicinal Chemistry," Beijing; Military Medical Science Press, 2011, National Secondary Health Vocational Education Task-Leading Planning Textbook p. 236 (5 pages).

(Continued)

*Primary Examiner* — James D. Anderson
(74) *Attorney, Agent, or Firm* — McNeill Baur PLLC

(57) ABSTRACT

The new compound 3-(1-(2,3-dichloro-4-methoxyphenyl) ethyl)-1-methyl-1-(1,3, 3-trimethylpiperidin-4-yl)urea monohydrochloride salt has a high capability to permeate through the blood-brain barrier and to display, at central nervous system level, a consistent ghrelin agonist activity; the compound is effective in the treatment and/or prevention of a medical condition mediated by the ghrelin receptor in the central nervous system. In particular, in experimental tests, the compound has shown high efficacy in the treatment of neurotoxic damage, with a useful combined pattern of neuroprotective effects both at central and peripheral level. The compound is further useful in the treatment of conditions which require a reduction of the heart rate. The compound is pharmacologically active at low to moderate doses, thus showing a favourable therapeutic index.

22 Claims, 12 Drawing Sheets

(56) References Cited

OTHER PUBLICATIONS

Moon et al., Neuroprotective Effect of Ghrelin in the 1-Methyl-4-Phenyl-1,2,3,6-Tetrahydropyridine Mouse Model of Parkinson's Disease by Blocking Microglial Activation, Neurotox Res (2009) 15:332-347 (16 pages).

Theil et al., "Suppression of Experimental Autoimmune Encephalomyelitis by Ghrelin," J Immunol. Aug. 15, 2009;183 (4):2859-66; https://doi.org/10.4049/jimmunol.0803362 (8 pages).

Zhang et al., "Ghrelin and Cardiovascular Diseases," Current Cardiology Reviews, 2010, 6, pp. 62-70 (9 pages).

* cited by examiner

Data obtained from Holter-ECG (mean from the average of triplicate readings)

CENTRALLY-ACTIVE GHRELIN AGONIST AND MEDICAL USES THEREOF

CROSS REFERENCE TO RELATED APPLICATIONS

This application is a national phase entry pursuant to 35 U.S.C. § 371 of International Application No. PCT/EP2019/056438, filed Mar. 14, 2019, which claims the benefit of priority of European Application No. 18163425.4, filed Mar. 22, 2018, each of which is incorporated by reference herein in its entirety for any purpose.

STATE OF THE ART

Ghrelin is a natural peptide hormone produced by ghrelinergic cells in the gastrointestinal tract which functions as a neuropeptide in the central nervous system. The biological target of ghrelin is the G protein-coupled growth hormone secretagogue receptor (GHSR), first cloned in 1996 (1). Two receptor subtypes have been described, 1a and 1b, but only the former is capable of activating signal transduction (2). GHSR is expressed primarily in the nervous system as well as in multiple non-nervous organs where it is involved in diverse physiological processes (2-4). The ghrelin peptide is mainly involved in the regulation of appetite, playing also a significant role in regulating the distribution and rate of use of energy. Ghrelin peptide acts on hypothalamic brain cells both to increase hunger, and to increase gastric acid secretion and gastrointestinal motility to prepare the body for food intake. Ghrelin peptide also plays an important role in regulating reward perception in dopamine neurons that link the ventral tegmental area to the nucleus accumbens (a site that plays a role in processing sexual desire, reward, and reinforcement, and in developing addictions) through its co-localized receptors and interaction with dopamine and acetylcholine. Clinical trials have evaluated the therapeutic potential of the ghrelin peptide in multiple disease states including anorexia nervosa (5), cancer cachexia (6,7), sleep-wake regulation (8), chronic heart failure (9), and gastrointestinal mobility disturbances (10). In animals, ghrelin promotes cell proliferation and neurogenesis in neurons (11). The ghrelin peptide has also been shown to possess neuroprotective properties and to prevent apoptosis (12). Ghrelin receptors (GHSRs) have been located in several distinct regions of the central nervous system (CNS). Exogenous administration of the ghrelin peptide ameliorates experimental encephalomyelitis (15), Parkinson's (16) and Alzheimer's disease (17) in preclinical models. In addition, the ghrelin peptide has been proposed to possess direct neural repair properties after central or peripheral nervous system injury (18). Neuropathic pain has an important inflammatory component, with sustained activation of neuroglial cells and increased production of pro-inflammatory cytokines. Moreover, there are reports of therapeutic effects of ghrelin peptide in rodent models of diabetic-(20), chronic constrictive injury-(21) and chemotherapy-induced neurotoxicity (CIPN) (22), as well as in acute pain (23), and chronic arthritis (24) models. However, the limited brain penetration of ghrelin peptide (25), its lack of oral bioavailability and its short half-life of only 8-24 minutes in rodents (26), and 37 min in man (27) limit its clinical utility as a drug. In fact, demonstration of preclinical efficacy often requires multiple systemic injections or central intrathecal/intraventricular administration, emphasizing the need for continuous infusion of ghrelin or use of agonists with longer half-lives and enhanced nervous system penetration.

The identification of the ghrelin receptor has prompted researches aimed at identifying new compounds with binding affinity to the said receptor, with ghrelin-like activity, looking for possible therapeutic advantages over the original peptide. Non-peptide small molecules would be here of particular interest as being likely to by-pass the peptide metabolic inactivation pathways; at the same time, however, the higher structural difference with the original peptide may possibly result in a variations in the original spectrum of activities of ghrelin and ghrelin-like molecules.

The patent application WO2012/116176 describes asymmetric ureas of general formula (I)

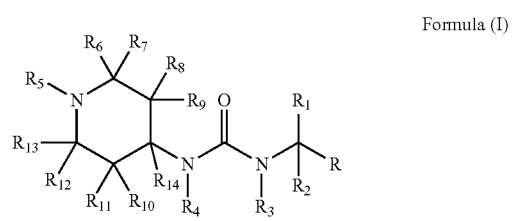

Formula (I)

having ghrelin receptor modulation properties; the application contains experimental data concerning the compound's GHSR1a receptor affinity and in-vivo activity on food intake in mice; the compounds are proposed for use in the treatment of a number of diseases including obesity, overweight, eating disorder, metabolic syndrome, wasting due to ageing or AIDS, gastrointestinal disease, gastric disorder, etc.

The patent application WO2015/134839 describes further ghrelin modulators of formula:

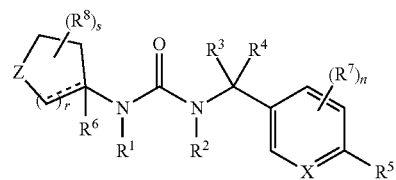

The application contains experimental data concerning the compound's GHSR1a receptor affinity and in-vivo activity on food intake and in alcohol abuse mice models.

Despite large efforts, none of the recently discovered small molecule agonists has yet been approved for therapeutic use. Their clinical utility is often limited by unsatisfactory safety profile and/or poor uptake in the central nervous system. In particular, the CNS impermeability of ghrelin agonists represents a serious limitation, in view of the fact that large part of ghrelin receptors are expressed in the central nervous system and many ghrelin-dependent diseases are, at least in part, centrally mediated. On the other side, making available molecules capable to efficiently pass through the blood-brain barrier is a complex task: a successful passage requires overcoming various critical steps, in particular: the uptake of the drug molecule from the systemic circulation by brain endothelial cells; the efficient internalization of the drug into said cells; the capacity of these cells to release the drug, in non-metabolized form, to the CNS compartment, in sufficiently high amounts to elicit the pharmacological response. Only a fine tuning/synergy of the above mechanisms may result in a flux of drug in active form through the barrier to the CNS target: in reality, only a minor fraction of known drug molecules are found in sensible amounts in the CNS after systemic administration: this does not surprise because the blood-brain barrier is functionally structured to isolate the CNS compartment from possibly dangerous xenobiotics present in the blood.

Moreover, for those medical conditions requiring action at both central and peripheral level, the finding of molecules capable to pass the blood-brain barrier faces is not as such an ideal solution: in fact, they face the further challenge of achieving/maintaining a suitable balance of drug in active form and active concentration both compartments across the barrier, such that any pharmacokinetic favored accumulation at central level does not compromise useful effects at peripheral level; this problem is particularly felt in the area of neurological diseases, which often involve damages at both central and peripheral level. Moreover the capability to pass the blood-brain barrier, while opening the way to the desired action at central level, raises new problems linked to a potentially excessive accumulation of drug in the brain; therefore an ideal brain-passing drug should be effective at very low doses, thus ensuring a balance between the accumulation/elimination processes, preventing the risk of brain accumulation in sensible amounts.

Therefore the need is still unmet for small-molecule, synthetic ghrelin agonists, having a strong affinity to the ghrelin receptor in the brain, being capable to pass the blood-brain barrier in significant amounts in non-metabolized form and to establish pharmacologically active concentrations in the brain. The need is further felt for ghrelin agonists, being particularly effective in the neurological area, showing a therapeutic effects at both peripheral and central level; an even further need is felt for ghrelin agonists having a reduced risk of undesired brain accumulation.

SUMMARY

The present Applicant has now found that the compound 3-(1-(2,3-dichloro-4-methoxyphenyl) ethyl)-1-methyl-1-(1, 3,3-trimethylpiperidin-4-yl)urea monohydro-chloride salt is a ghrelin agonist with a high capability to permeate through the blood-brain barrier and to display, at central nervous system level, a remarkable ghrelin agonist activity; the compound is therefore effective in the treatment and/or prevention of a medical condition mediated by the ghrelin receptor in the central nervous system. In particular, experimental test have elicited a high efficacy in the treatment of neurotoxic damage, with a useful combined pattern of neuroprotective effects both at central and peripheral level. The compound also produces a centrally-mediated bradycardic effect, so far unknown for ghrelin-like molecules, making it particularly useful in the treatment of cardiovascular conditions which require a reduction of the heart rate. The compound further shows a non-linear dose/efficacy ratio, being maximized at intermediate, instead than highest dose levels: this allows to reach the maximum desired effects while administering moderate doses, thus limiting the risks of unwanted brain accumulation in the brain or other body compartments, as well as any other general toxicity issues.

DETAILED DESCRIPTION

Figure 1:
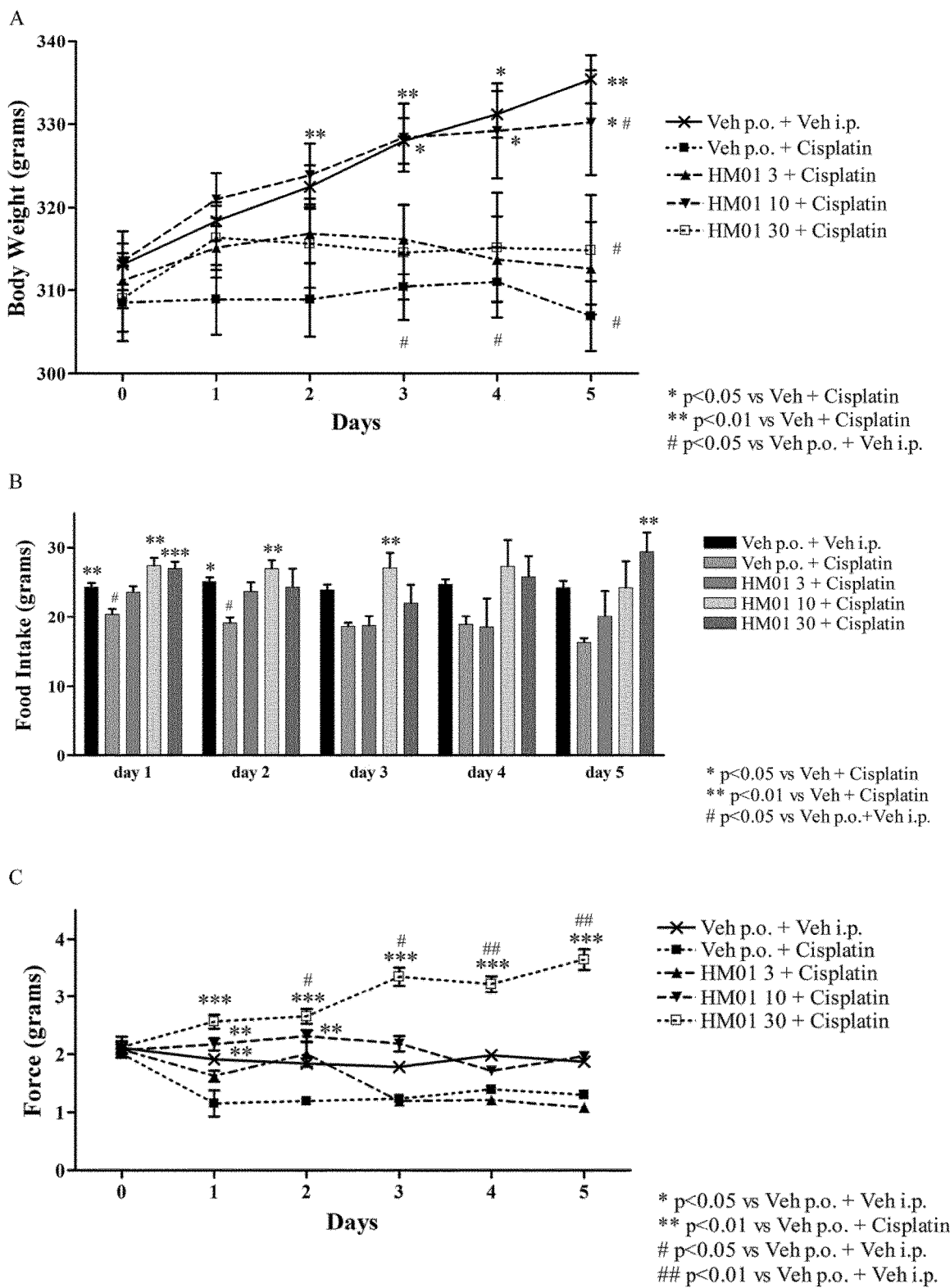
FIG. 1: Effect of Compound A treatment on body weight, food intake and mechanical hyperalgesia induced by cisplatin injection into rats. Cisplatin (0.5 mg/kg), administered IP once daily for 3 days (day 0 thru Day2), resulted in a decrease in body weight and daily food intake and development of mechanical hyperalgesia. A) One way ANOVA followed by post hoc Tukeys multi-comparison test found a significant overall effect of cisplatin on body weight ($p<0.05$) which was improved by Compound A treatment at 3, 10 (both $p<0.01$) and 30 mg/kg ($p<0.05$). B) Food intake was significantly reduced by cisplatin ($p<0.05$) and this was improved by 10 and 30 mg/kg Compound A (both $p<0.05$). C) Mechanical hyperalgesia was induced by cisplatin and significantly improved by 10 and 30 mg/kg Compound A ($p<0.05$), but not 3 mg/kg Compound A.

The compound 3-(1-(2,3-dichloro-4-methoxyphenyl) ethyl)-1-methyl-1-(1,3,3-trimethylpiperidin-4-yl)urea monohydrochloride salt object of the present invention is herein referred briefly as "Compound A". It has the following structural chemical formula:

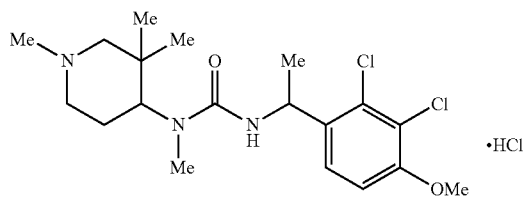 [SMILES: COc1ccc(C(C)NC(=O)N(C)C2CCN(C)CC2(C)C)c(Cl)c1Cl ; Cl]

The term "medical condition" used herein refers to diseases or disturbs; the term "disease" means an established medical syndrome; the term "disturb" means any damage or malfunctioning of a particular body part, organ or tissue which may occur with or without giving rise to a complete pathological syndrome.

The term "medical condition mediated by the ghrelin receptor in the central nervous system" means those diseases/disturbs being typical or at least partly typical of the central nervous system, which respond to the treatment with ghrelins; among them there can be mentioned encephalomyelitis, Parkinson's Disease, Alzheimer's Disease and cognitive disorders; in particular, Compound A is highly effective on neuropathy, neuropathic pain and/or neurodegeneration; in addition, compound A also shows an unexpected bradycardic activity useful in the context of diseases requiring a reduction of heart rate (tachycardia), for example occurring in case of chemotherapy-induced cardiovascular toxicity; tachycardia is part of the class of central nervous system diseases, as it responds to vagal nerve control. When used to treat neuropathy, this is preferably a chemotherapy-induced neuropathy, being present at central and/or peripheral levels. Chemotherapeutic agents are well-known known in the art: typically, but not limitedly, they are alkylating agents or proteasome inhibitors (32). Among the alkylating agents there can be mentioned platinum complexes like e.g. cisplatin, carboplatin, etc. Among the proteasome inhibitors there can be mentioned bortezomib, carfizomib, ixazomib, oprozomib, delanzomib, marizomib, MG-132, ONX-0914, VR-23, celastrol, epoxomicin, etc.

The term "ghrelin receptor" is well-known in the art, also with its alternative name "growth hormone secretagogue receptor" or "GHS receptor"; all these synonyms are meant to be equivalent and can be used herein interchangeably; the term ghrelin receptor and its synonyms extend to all its possible forms (for example the GHS1 form) as well as all its isoforms (for example the isoforms GHS1a, GHS1b, etc.).

The terms "treating" and "treatment," when used herein, refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The invention provides a method of treating or preventing one or more medical conditions (i.e. diseases or disturbs) mediated by the ghrelin receptor in the central nervous system, characterized by administering Compound A to a patient in need thereof.

A further object of the invention is the Compound A for use in treating or preventing one or more medical conditions (diseases or disturbs) mediated by the ghrelin receptor in the central nervous system.

A further object of the invention is the use of Compound A in the manufacture of a medicament for treating or preventing one or more medical conditions (diseases or disturbs) mediated by the ghrelin receptor in the central nervous system.

A further object of the invention is a method to favour absorption into the central nervous system of a ghrelin agonist in a patient in need thereof, characterized by administering to said patient, a therapeutically effective amount of Compound A as ghrelin agonist.

A further object of the invention is a method to favour the establishment of therapeutically active concentrations of a ghrelin agonist in the central nervous system of a patient in need thereof, characterized by administering to said patient, a therapeutically effective amount of Compound A as ghrelin agonist.

As used herein, the term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

Compound A, i.e. 3-(1-(2,3-dichloro-4-methoxyphenyl) ethyl)-1-methyl-1-(1,3,3-trimethyl-piperidin-4-yl)urea monohydrochloride salt is a new compound; the corresponding free base was described in the patent application WO2012/116176. Accordingly, the invention includes Compound A per se, its use in medicine, and pharmaceutical compositions comprising it; the invention further includes a process of producing Compound A, characterized by reacting its free base with hydrochloric acid, as shown in the experimental part.

As further shown in the experimental part, Compound A has an interesting purity, stability and solubility profile, which makes it particularly suitable for formulation in a variety of pharmaceutical forms under different manufacturing conditions, with no appreciable decrease in purity and potency. The invention thus extends to Compound A in crystalline form, in particular in the specific crystalline form having the pattern of XRDP peaks shown in FIG. 9. Also thanks to these properties, Compound A can be freely formulated in any pharmaceutical form as required by the chosen medical treatment. Forms adapted for systemic administration are preferred. For example, it can be formulated as a tablet, pill, capsule, microcapsule, granule, microgranule, pellet, micropellet, powder, lyophilized powder, solution, suspension or emulsion, gel, cream, percutaneous or transdermal delivery system, etc.

Compound A is preferably administered in dose amount ranging from about 0.03 mg to about 10 mg., preferably from about 0.1 mg to about 2 mg, based on the weight of the free base. These dosages are meant to be daily doses, for an average adult patient. They can be varied and/or adapted in function of the degree of severity of the diseases, the specific patient conditions, the specific administration route chosen, etc.

The route of administration of Compound A is a systemic one: thanks to its the blood-brain barrier penetrating ability, in order to target the central nervous system it is not necessary to inject it directly into the central nervous system or into the brain; it is in fact sufficient that the drug reaches the general circulation via one conventional systemic administration route, e.g. oral, peroral, buccal, inhalatory, rectal, etc.: once circulating in the bloodstream, Compound A is taken up by the endothelial cells of the central nervous system and from there it is released in active form into the central nervous system. It is thus possible to treat diseases mediated by the ghrelin receptor in the central nervous system, without recurring to invasive administration routes which provide direct access to the central nervous system (e.g. intratechal, intraspinal, etc.). Advantageously, according to the invention, the invasive administration routes directly into the central nervous system can be avoided; therefore the methods of administration contemplated by the present invention can also be characterized as: "peripherally to the central nervous system" or "externally to the central nervous system".

Various pharmaceutical compositions can be developed that make use of the present Compound A. The composition can be suitable for administration by any appropriate route, for example, orally, parenterally, or intravenously, in liquid or solid form. Preferred routes of administrations are injectable and/or oral. These compositions will generally include an inert diluent or an edible carrier. They may be enclosed in gelatin capsules (for oral use) or compressed into tablets (for oral or buccal use) or formulated into troches (for buccal use). For these purposes, the active compound can be incorporated with excipients and used in the form of tablets, troches, or capsules. Pharmaceutically compatible binding agents, and/or adjuvant materials can be included as part of the composition.

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a gliding such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, orally disintegrating film, orally disintegrating tablet, chewing gum. A syrup may contain, in addition to the active compounds, sucrose as a sweetening agent and certain preservatives, dyes and colorings and flavors.

Solutions or suspensions used for injection can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride, mannitol and dextrose. An injectable preparation, can be enclosed in ampoules, disposable syringes or multiple dose vials made of glass or plastic.

The invention is described next with reference to the following non-limiting examples.

EXPERIMENTALS

Example 1

Synthesis and Characterization of (3-(1-(2,3-dichloro-4-methoxyphenyl) ethyl)-1-methyl-1-(1,3,3-trimethylpiperidin-4-yl)urea monohydrochloride (Compound A)

1.63 Kg of (3-(1-(2,3-dichloro-4-methoxyphenyl) ethyl)-1-methyl-1-(1,3,3-trimethylpiperidin-4-yl)urea dried product, previously obtained by the synthetic procedure described in WO2012/116176, was dissolved in 11.2 Kg of acetone at 22° C.±3° C. The solution was filtered over 1 micron filter bag as polish filtration and the filter was washed with acetone (1.6 Kg). Hydrochloric acid 4M (1.2 Kg) in water was added on the filtered solution maintaining the internal temperature of 22° C.±3° C. The obtained suspension was stirred at 22° C.±3° C. for at least 2 hours. Then the product was isolated by centrifugation and washed with acetone (1.6 Kg). 1.5 Kg of wet product was obtained. It was dried under vacuum at 60° C.±5° C. for at least 18 hours giving 1.4 Kg of 3-(1-(2,3-dichloro-4-methoxyphenyl) ethyl)-1-methyl-1-(1,3,3-trimethylpiperidin-4-yl)urea monohydrochloride (Compound A) as a white to off white crystalline powder. Purity (HPLC) min. 98%.

Figure 9:
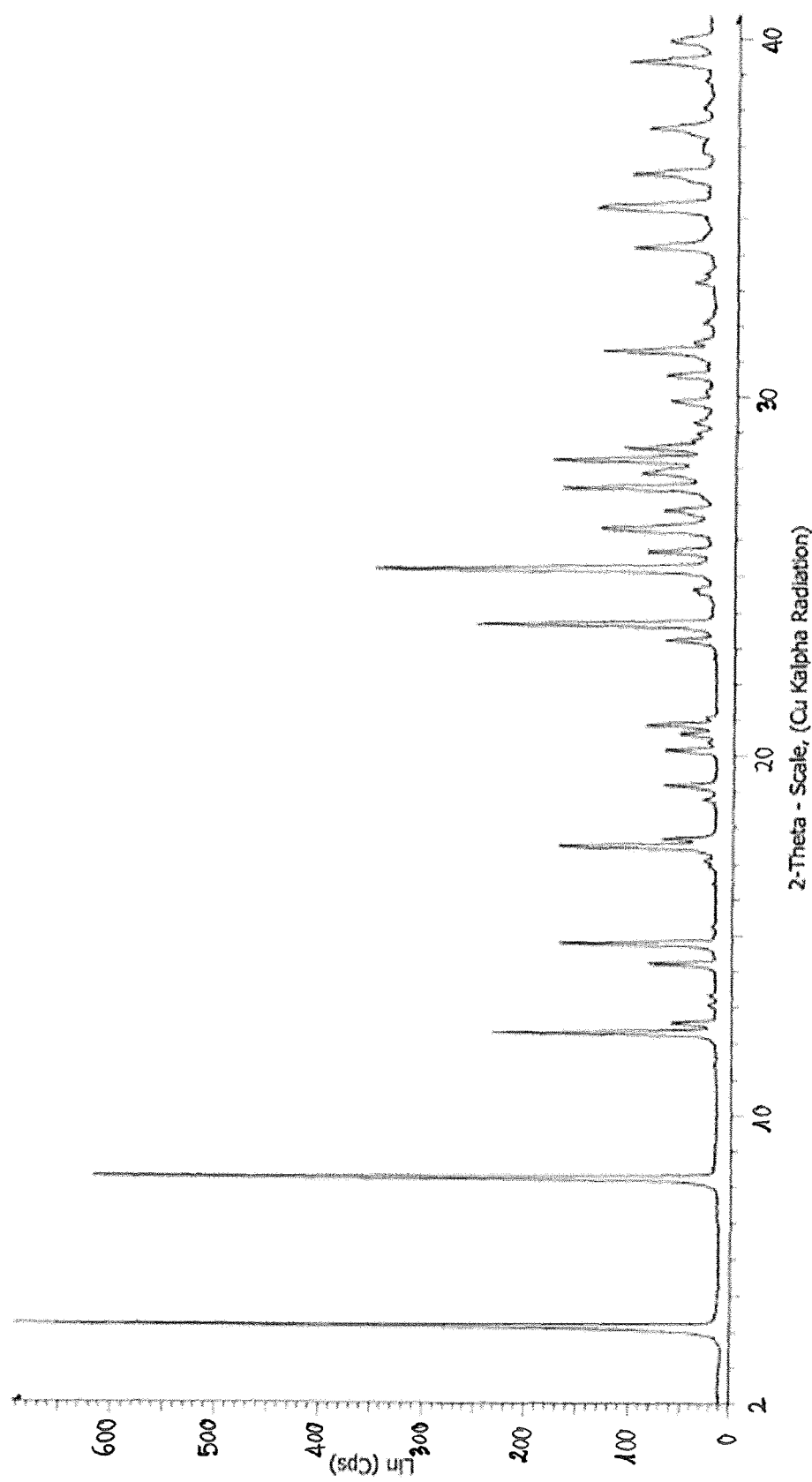
FIG. 9: XRPD data of compound A.
Figure 10:
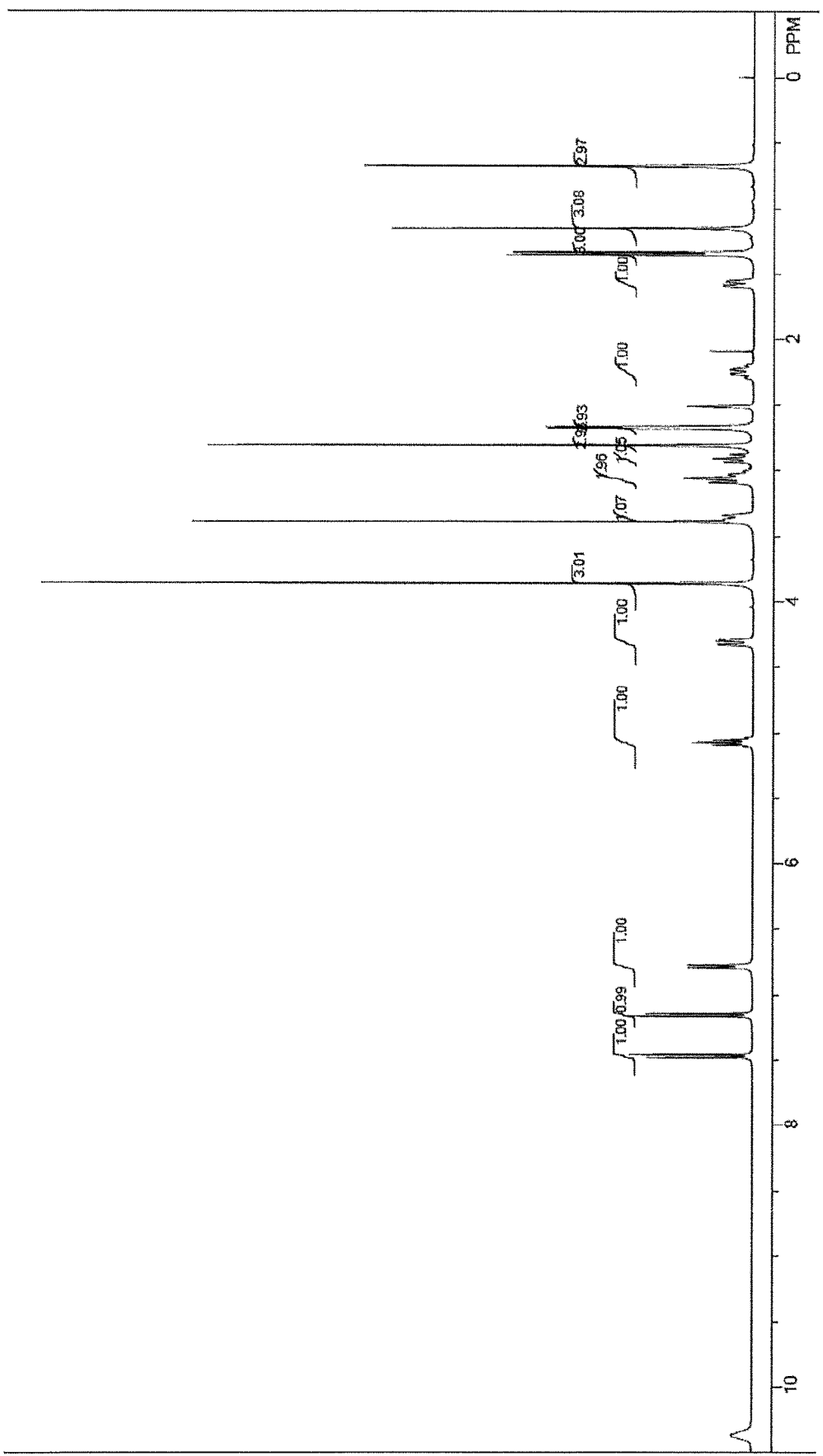
FIG. 10: $^1$H-NMR of Compound A.
Figure 11:
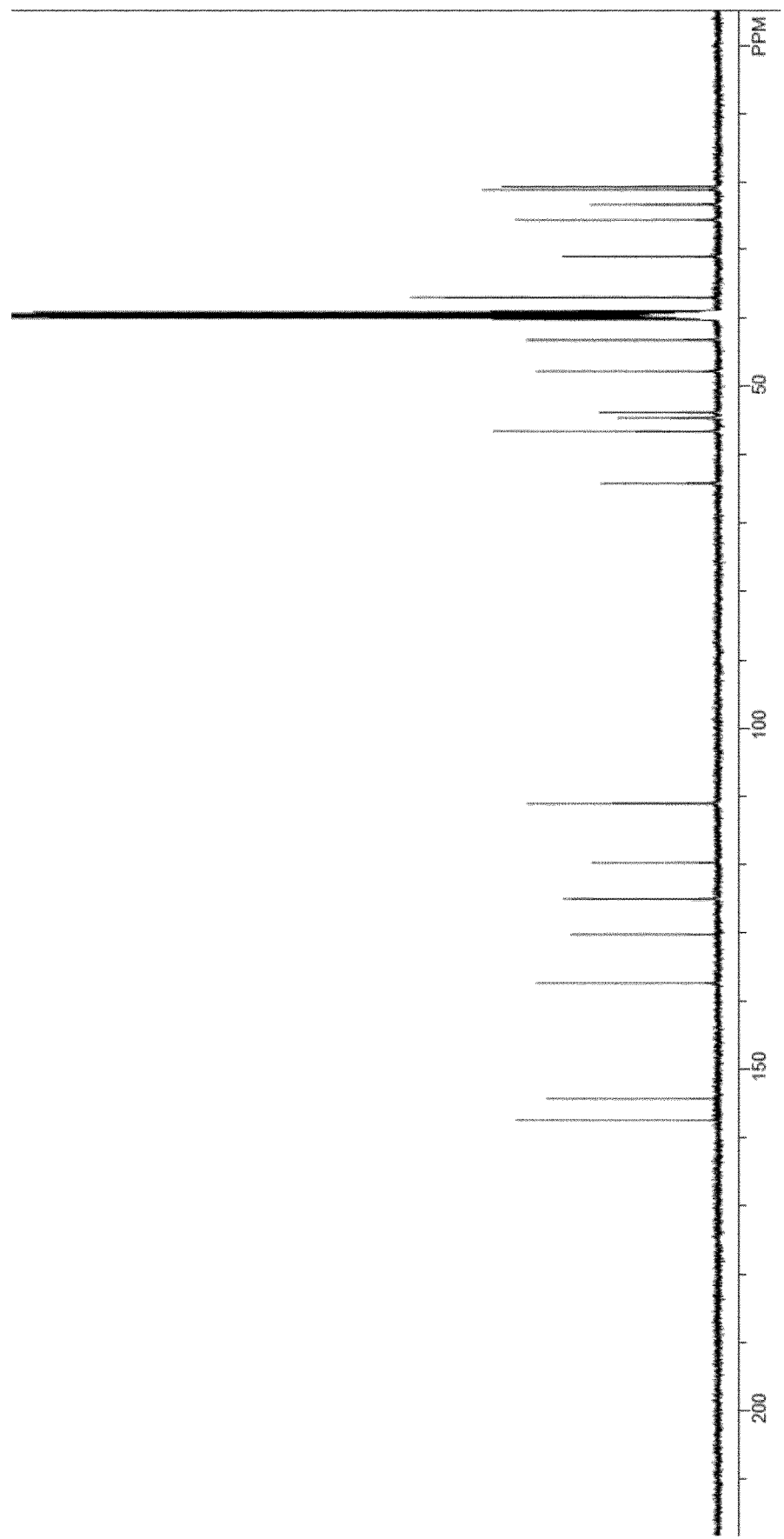
FIG. 11: $^{13}$C-NMR of Compound A.

The XRPD, $^1$H-NMR, $^{13}$C-NMR characterization of Compound A is shown in FIGS. 9-11.

Example 2 Water Solubility Testing

The Compound A showed solubility in water at room temperature of about 33 mg/mL. As a reference, the corresponding fumarate salt has solubility of only 10 mg/mL; the corresponding free base showed a solubility well below 2 mg/mL.

Example 3 Stability Testing

The stability of Compound A was followed by HPLC analysis. In the following tables the data collected during the storage of the wet, as well as during drying at laboratory scale. Additionally a stability study was performed over 3 years on industrial batch of dried material.

| Stability of crude wet material Compound A at 2-8° C. and at room temperature under air: | | | | | |
|---|---|---|---|---|---|
| Compound A (batch #01) HPLC results at 2-8° C. | | | Compound A (batch #02) HPLC results at rt | | |
| t = 0 | t = 8 days | t = 30 days | | t = 0 | t = 24 days |
| Compound A 99.60% | 99.70% | 99.75% | Compound A | 99.74% | 99.73% |
| Impurity RRT 0.97 0.40% | 0.29% | 0.25% | Impurity RRT 0.97 | 0.24% | 0.27% |

According to the results, we did not observe any degradation of Compound A over more than 4 weeks of storage of the wet powder at 2-8° C. In the same way, the sample stored at room temperature for 24 days, after being hold in the fridge for 36 days, did not show any degradation in HPLC.

| Stability of crude dried material Compound A at 25° C./ 60% R.H. (relative humidity): | | | | | | | |
|---|---|---|---|---|---|---|---|
| HPLC stability results at 25° C./ 60% R.H. | | | | | | | |
| 0 | 3 | 6 | 9 | 12 | 18 | 24 | 36 |
| Compound A 100.0% | 100.0% | 100.0% | 99.9% | 100.0% | 100.0% | 100.0% | 100.0% |
| Total Impurities <0.05% | <0.05% | <0.05% | 0.10% | <0.05% | <0.05% | <0.05% | <0.05% |

According to the results, we did not observe any degradation of Compound A over 3 years of storage of the dried product at 25° C./60% R.H.

| Stability of crude dried material Compound A during drying at 60° C. | | |
|---|---|---|
| | HPLC results | |
| | t = 0 | t = 74 hours |
| Compound A | 99.83% | 99.78% |
| Impurity RRT 0.97 | 0.17% | 0.17% |

According to the results, we observed that the material was stable during drying at 60° C. for 74 hours.

Example 4 Evaluation of Ghrelin Agonistic Activity of Compound A

HEK293 cells stably expressing human GHSR1a receptor were used in FLIPR assay. Cells were maintained under standard procedures. One day prior the test, cells were seeded at a density of 1.5×10$^4$/well in a Matrigel® coated 384-well plate with 30 μl of complete DMEM medium, and incubated at 37° C. in 5% CO2 for 22-26 hrs. On the test day, 4× loading dye was added into each well (10 μl per well for 384 well plates). Assay plates were incubated at 37° C. in the dark for 30 minutes. Then the dye content was removed by centrifugation at 300 rpm for 30 s. 40 μL HBSS/Hepes with 1 mM probenicid was added with Platemate Matrix (low speed setting, Thermo). The plate was then placed in FLIPR Tetra (Molecular Device) and 5× working concentrations of agonists were added by FLIPR. Fluorescence signal was detected with FLIPR at room temperature according to standard settings.

Compound A displayed strong agonist activity in FLIPR assays, with an $EC_{50}$ of 1.25±0.42 nM In additional binding study, compound A was dissolved in DMSO and diluted with water in different range of concentrations. Membrane protein prepared from BHK cells stably expressing human GHSR1 receptor were used for binding assay. The membrane was diluted in assay buffer to yield 20 μg/well in 120 μl. The binding assay was set up in 96 well plate as following: 120 μl [$^{125}$I]Ghrelin (final concentration 1 nM) and 15 μl compound A (10×) diluted in the assay buffer. The reaction mixture was incubated at room temperature for 30 minutes before terminating by quick filtration onto GF/B filtration plate pre-soaked in 0.3% PEI using cell harvester (Perkin Elmer). The filter was washed three times and dried at 37° overnight. The radioactivity bound to filter membrane was measured with MicroBeta Trilux (Perkin Elmer). Compound A displayed strong affinity to GHSR1 A receptor in [$^{125}$I]Ghrelin binding assay, with Ki value of 1.42±0.35 nM)

Example 5

Pharmacokinetic Studies and Assessment of Brain Penetration of Compound A

Figure 12:
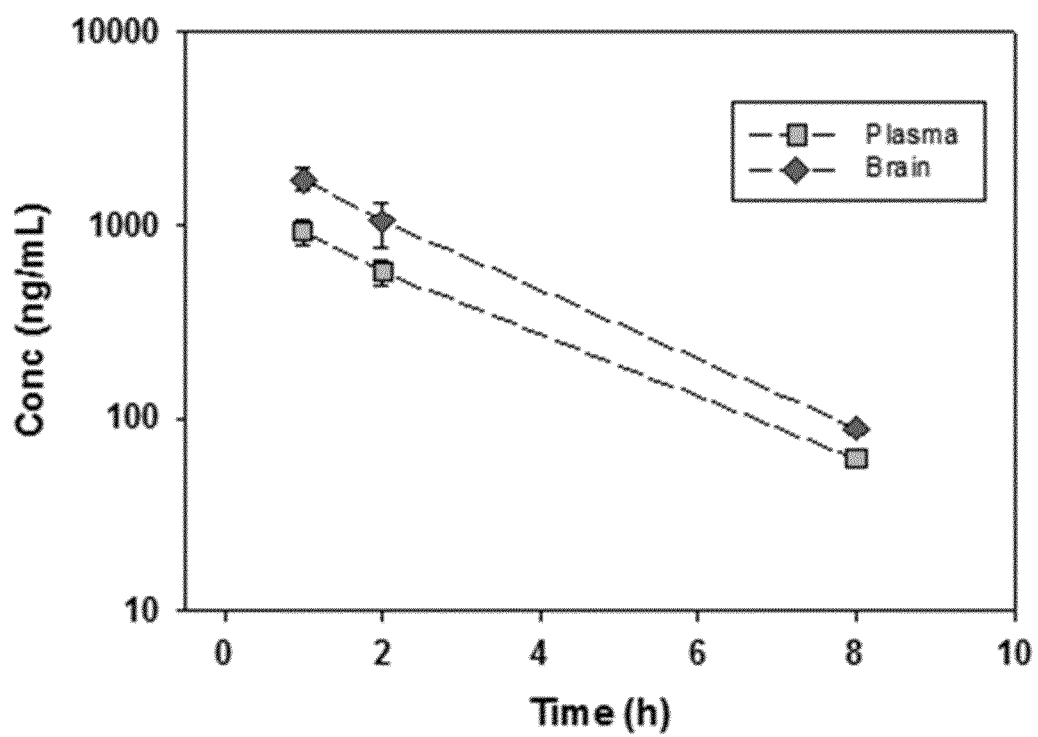
FIG. 12: Mean concentrations of Compound A in plasma (ng/mL) and brain (ng/g) after single IV 10 mg/kg to male Sprague Dawley rats.

After single 10 mg/kg IV administration of Compound A to Sprague Dawley rats, the compound was rapidly cleared from the systemic circulation and distributed into tissues and organs. The bioanalysis of Compound A in plasma and brain was performed by LC-MS-MS methods and the pharmacokinetic analysis was performed by standard non-compartmental approach. In this test, the concentrations of Compound A measured in the brain at 10 mg/kg at 1, 2 and 8 h post-dosing were found to be 1.5 to 1.9-fold higher than those in plasma and both curves decayed in parallel with the corresponding plasma curve. Mean concentrations of Compound A in plasma (ng/mL) and brain (ng/g) after single IV 10 mg/kg to male Sprague Dawley rats are reported in FIG. 12. Interestingly, the higher concentration of compound A in the brain decayed in parallel with plasma concentration: this shows that this compound, while having a useful higher brain affinity, does not accumulate therein, thus avoiding risks of local brain toxicity.

In detail, after single oral administration at the doses of 3, 10 and 30 mg/kg, the bioavailability of Compound A was high and exceeded 80%. After both single IV and oral administrations, the exposure to Compound A increased with the dose in the range of doses tested. The summary of pharmacokinetic data obtained from rats administered orally or intravenously with Compound A is reported as follows:

| | | IV | | Oral | | |
| | | Dose | | | | |
| Parameter | Units mg/kg | 3 | 10 | 3 | 10 | 30 |
|---|---|---|---|---|---|---|
| $C_{0083}/C_{max}$ | ng/mL | 682 ± 58.5 | 2360 ± 460 | 181 ± 43.7 | 585 ± 175 | 1430 ± 208 |
| $t_{max}$ | h | — | — | 1.67 ± 0.577 | 1.67 ± 2.02 | 1.67 ± 0.577 |
| $AUC_{last}$ | ng · h/mL | 937 ± 145 | 3540 ± 765 | 780 ± 155 | 3400 ± 1010 | 12300 ± 1400 |
| $t_{1/2, z}$ | h | 1.92 ± 0.121 | 1.81 ± 0.156 | 2.56 ± 0.177 | 3.45 ± 0.0495 | 3.26 ± 0.170 |
| CL (clearance) | mL/min/kg | 52.0 ± 9.22 | 46.8 ± 11.2 | — | — | — |
| $V_{ss}$ (volume distribution at steady state) | mL/kg | 6600 ± 491 | 5910 ± 896 | — | — | — |
| F (bioavailability) | % | — | — | 83 ± 21 | 96 ± 35 | 116 ± 28 |

In further studies, the pharmacokinetics of Compound A was compared to that of two reference compounds, previously described in the patent application WO2012/116176. The obtained data are as follows:

Reference 1

| Species | Structure | Dose Rout | Doseing level (mg/kg) | AUC (0-t) Ng/ml*h | Vz/F L/kg | CLz/F L/h/kg |
|---|---|---|---|---|---|---|
| Rat | 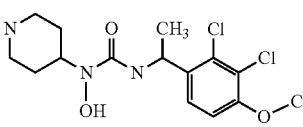 (RS) | IV | 3 | 1740.8 | 7.6 | 1.7 |
| | | PO | 3 | 362.4 | 25.8 | 4.5 |
| Dog | | IV | 1 | 2320.2 | 5.9 | 0.3 |
| | | PO | 2 | 4441.8 | 4.6 | 0.4 |

| | T1/2 z | Tmax | Cmax | F | 2 hr Brain/Plasma Ratio | |
| Species | h | h | ng/ml | (%) | Ratio | ng · g/ng/ml |
|---|---|---|---|---|---|---|
| Rat | 3 | | 439.1 | | 0.3 | 61.7/207.1 |
| | 3.4 | 4 | 45.3 | 20.8 | | |
| Dog | 12.1 | | 562.1 | | | |
| | 7.6 | 0.5 | 576.9 | 95.7 | | |

Reference 2

| Species | Structure | Dose Rout | AUC (0-t) Ng/ml*h | Vz/F L/kg | CLz/F L/h/kg | t1/2 z h |
|---|---|---|---|---|---|---|
| Rat | (SH) | IV | 8412.7 | 2.8 | 0.3 | 5.8 |
|  |  | PO | 6139.8 | 3.3 | 0.4 | 6.1 |
| Dog |  | IV | 14810.5 | 1.1 | 0.04 | 22.2 |
|  |  | PO | 28288.2 | 0.9 | 0.06 | 11.8 |

| Species | Tmax h | Cmax ng/ml | F (%) | 2 hr Brain/Plasma Ratio Ratio | ng · g/ng/ml |
|---|---|---|---|---|---|
| Rat |  | 1223.0 |  | .10 | 79.6/790.3 |
|  | 6.0 | 480.8 | 73.0 |  |  |
| Dog |  | 1520.9 |  |  |  |
|  | 0.67 | 2037.9 | 95.5 |  |  |

Compound A (Invention)

| Species | Structure | Dose Rout | Doseing level (mg/kg) | AUC (0-t) Ng/ml*h | Vz/F L/kg | CLz/F L/h/kg |
|---|---|---|---|---|---|---|
| Rat | 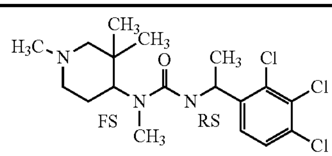 | IV | 3 | 701.5 | 9.9 | 4.2 |
|  |  | PO | 3 | 495.3 | 38.6 | 3.9 |
| Dog |  | IV | 1 | 598.7 | 3.7 | 1.6 |
|  |  | PO | 2 | 373.1 | 13.0 | 5.7 |

| Species | T1/2 z h | Tmax h | Cmax ng/ml | F (%) | 2 hr Brain/Plasma Ratio Ratio | ng · g/ng/ml |
|---|---|---|---|---|---|---|
| Rat | 1.6 |  | 468.4 |  | 1.44 | 172./119.3 |
|  | 12.7 | 3.3 | 58.6 | 70.6 |  |  |
| Dog | 1.6 |  | 379.7 |  |  |  |
|  | 1.6 | 1.5 | 114.8 | 31.2 |  |  |

The above data show that the tested reference compounds, 2 hours after intravenous administration failed to reach therapeutically meaningful concentrations in the brain; by contrast, Compound A reached a 2-fold or 3-fold higher concentration (172 ng/g). Particularly interesting is the brain/blood ratio, giving an indication of how selectively the administered dose is directed throughout the blood-brain barrier and accumulates in the brain, compared with the fraction remaining in the bloodstream: the two reference compounds only showed a 0.1/0.3 brain/blood ratio, showing a poor brain permeability, the administered dose remaining substantially in the bloodstream. By contrast, Compound A showed a 1.4 brain/blood ratio: this shows a much stronger affinity of Compound A to the brain compartment such that, after just 2 hours after systemic administration, a significant fraction of the administered dose is found in the brain; the brain uptake is yet not total, which allows the drug to display in part useful activities at peripheral level. This is of particular utility in case of neurological diseases which, besides a damage at the CNS level, also involve peripheral nerve degeneration and require a reparative action at such level. Without being bound by theory, it appears that the high brain penetration of Compound A may be due to its ability of not being P-gp substrate, which is the efflux pump system preventing molecules to pass the blood-barrier.

Further pharmacokinetic data are presented in the table below:

| Compound A-Pharmacokinetics following acute and chronic dosing | | | | | |
|---|---|---|---|---|---|
| ACUTE DOSING | | | | | |
| $C_{max}$ (pmol/mL or pmol/g) | Tmax (h) | $t_{1/2}$ (h) | $AUC_{0-t}$ (h*pmol/ mL or h*pmol/g) | $AUC_{0-\infty}$ (h*pmol/ mL or h*pmol/g) | Tissue penetration index (Tissue/plasma ratio) |
| 10 mg/kg | | | | | |
| Plasma 1150 | 0.25 | 0.90 | 945.2 | 960.7 | 1 |
| Sciatic nerve 1550 | 0.25 | 4.7 | 2923 | 2984.3 | 3.1 |
| DRG 1713 | 0.25 | NR* | 4296 | 4357.8 | 4.5 |
| 30 mg/kg | | | | | |
| Plasma 2726.8 | 0.25 | 1.1 | 4335.9 | 4375.2 | 1 |
| Sciatic nerve 4966.1 | 0.5 | 4.7 | 14220.3 | 14546.6 | 3.3 |
| DRG 4406.7 | 0.5 | NR** | 12247.3 | 12380.6 | 2.8 |

| CHRONIC DOSING | | | | | |
|---|---|---|---|---|---|
| Dose | Plasma pmol/mL | Sciatic pmol/g (pooled) | DRG Nerve pmol/g (pooled) | Tissue penetration index (SN/plasma ratio) | Tissue penetration index (DRG/plasma ratio) |
| 10 mg/kg | 703 (±52) | 6274 | 12386 | 8.9 | 17.6 |
| 30 mg/kg | 3113 (±548) | 37346 | 58819 | 12.0 | 18.9 |

*NR (not reported) when correlation coefficient for terminal elimination <0.9
SN = sciatic nerve;
DRG = dorsal root ganglia Example 6

Effects of Compound A on In-Vivo Animal Neurotoxicity Models

Drugs and Formulations

Compound A was made as a suspension in 0.5% carboxymethylcellulose solution in dosing volumes of 1 and 10 mL/kg for rats and mice respectively and dosed orally at 3, 10 or 30 mg/kg. Cisplatin was dosed in saline at 0.5 mg/kg intraperitoneally (i.p., 1 mL/kg). Oxaliplatin was formulated in 5% dextrose solution and injected i.p. (10 mL/kg) at a concentration of 0.6 mg/mL. Bortezomib was prepared in 10% Tween 80, 10% EtOH 100% and 80% saline solution and injected i.v. (1 mL/kg) at 0.2 mg/kg. All dosing solutions were made fresh on each administration day.

Cisplatin Study

Fifty male Wistar rats weighing 250-300 g at start of experiment were randomly divided into 5 groups of 10 rats each. Group 1 received daily Compound A vehicle (p.o.) for 6 days and cisplatin vehicle (i.p.) for 3 days. Group 2 received Compound A vehicle (p.o) and 0.5 mg/kg cisplatin (i.p.) for 3 days followed by Compound A vehicle for 3 additional days. Group 3 received daily 3 mg/kg Compound A (p.o) and 0.5 mg/kg cisplatin (i.p.) for 3 days followed by 3 mg/kg Compound A for an additional 3 days. Group 4 received 10 mg/kg Compound A (p.o) and 0.5 mg/kg cisplatin (i.p.) for 3 days followed by 10 mg/kg Compound A for an additional 3 days. Group 5 received daily 30 mg/kg Compound A (p.o.) and 0.5 mg/kg cisplatin (i.p.) for 3 days followed by 30 mg/kg Compound A for an additional 3 days. In each case, cisplatin or cisplatin vehicle was dosed 30 min after Compound A or Compound A vehicle, which was dosed 1 hour prior to von Frey filament testing. Individual body weights and 24 h food intake were measured daily from just prior to initiation of dosing.

Oxaliplatin Study

Sixty female Balb/C mice weighing 20-25 g at start of experiment were used and divided into 4 groups of 15 mice each. Group 1 received Compound A vehicle (p.o.) daily, 60-90 min prior to oxaliplatin vehicle dosing (i.p.) twice weekly for 4 weeks. Group 2 received Compound A vehicle (p.o) daily, 60-90 min prior to 6 mg/kg oxaliplatin (i.p.) twice weekly for 4 weeks. Group 3 received 10 mg/kg Compound A (p.o) daily 60-90 min prior to 6 mg/kg oxaliplatin (i.p.) twice weekly for 4 weeks. Group 4 received 30 mg/kg Compound A (p.o.) daily 60-90 min prior to 6 mg/kg oxaliplatin (i.p.) twice weekly for 4 weeks. Body weights were measured daily, immediately prior to the initiation of dosing. Nerve conduction velocity (NCV) and potential amplitude measurements were made 24 h after last oxaliplatin (or vehicle) dose and 1 h after last Compound A (or vehicle) dose, after which blood, tissue samples (DRG, sciatic nerve [SN], and foot pads) were collected for pharmacokinetic and IENFD evaluations.

Bortezomib Studies

Prevention paradigm: Fifty-six Female Wistar rats weighing 200-225 g at start of experiment were randomized into 5 experimental groups. Group 1 was left untreated (CTRL, n=10), Group 2 was treated with bortezomib i.v. 0.2 mg/kg, 3 times/week for 8 weeks (BTZ, n=10), Group 3 was co-treated with bortezomib i.v. 0.2 mg/kg, 3 times/week for 8 weeks and Compound A p.o. 3 mg/kg daily 90 min before the i.v. co-administration of bortezomib (BTZ+Compound A 3, n=12), Group 4 was co-treated with bortezomib i.v. 0.2 mg/kg, 3 times/week for 8 weeks and Compound A p.o. 10 mg/kg daily 90 min before the i.v. co-administration of bortezomib (BTZ+Compound A 10, n=12), Group 5 was co-treated with bortezomib i.v. 0.2 mg/kg, 3 times/week for 8 weeks and Compound A p.o. 30 mg/kg daily 90 min before the i.v. co-administration of bortezomib (BTZ+Compound A 30, n=12). At baseline and after 8 weeks of treatment, caudal and digital nerve conduction and potential amplitude studies, behavioral tests (Dynamic) and blood collection to study proteasome inhibition were performed. After 8 weeks of treatment, tissue samples (sciatic and caudal nerves, DRG and foot pads) were collected and analyzed to study morphological parameters and intraepidermal nerve fibre density (IENFD).

Therapeutic paradigm: Fifty-six female Wistar rats weighing 200-225 g at start of experiment were randomized into 5 experimental groups. Group 1 was left untreated (CTRL, n=10), Group 2 was treated with bortezomib i.v. 0.2 mg/kg, 3 times/week for 8 weeks (BTZ, n=10), Group 3 was treated with bortezomib i.v. 0.2 mg/kg, 3 times/week for 4 weeks and co-treated with bortezomib 0.2 mg/kg, 3 times/week and Compound A p.o. 3 mg/kg daily 90 min before the i.v. co-administration of bortezomib for 4 weeks (BTZ+Compound A 3, n=12), Group 4 was treated with bortezomib i.v. 0.2 mg/kg, 3 times/week for 4 weeks and co-treated with bortezomib 0.2 mg/kg, 3 times/week and Compound A p.o. 10 mg/kg daily 90 min before the i.v. co-administration of bortezomib for 4 weeks (BTZ+Compound A 10, n=12), Group 5 was treated with bortezomib i.v. 0.2 mg/kg, 3 times/week for 4 weeks and co-treated with bortezomib 0.2 mg/kg, 3 times/week and Compound A p.o. 30 mg/kg daily 90 min before the i.v. co-administration of bortezomib for 4 weeks (BTZ+Compound A 30, n=12). At baseline and after 8 weeks of treatment, caudal and digital nerve conduction and potential amplitude studies and blood collection to study proteasome inhibition were performed. Behavioral tests (Dynamic) were performed after 4 and 5 weeks of bortezomib treatment. After 8 weeks of treatment, sciatic nerves, caudal nerves, DRG and foot pads were collected from all animals and analyzed to study morphological parameters and IENFDs.

Assessments

Von Frey Testing

In the cisplatin study, rats were individually housed and acclimated to handling and to the Von Frey testing apparatus for several days prior to start of the experiment. Baseline measurements were obtained prior to dosing. Behavioral testing was conducted following procedures previously described (28). Each filament was tested 5 times and the test continued until 3 withdrawal responses to a particular filament were recorded.

Dynamic Aesthesiometer Test

In the bortezomib studies, the mechanical nociceptive threshold was assessed using a Dynamic Aesthesiometer Test (model 37450, Ugo Basile Biological Instruments, Comerio, Italy). The mechanical threshold was assessed alternatively on each side every 2 minutes on 3 occasions to yield a mean value. The results represented the maximal pressure tolerated by the animals.

Nerve Conduction Studies (NCS)

NCV and potential amplitude measurements in the caudal and digital nerves were determined as previously described in mice (29) and rats (30). Baseline NCS measurements were performed prior to drug dosing. Animals were then randomly assigned to one of the study treatment groups with similar mean NCS values. NCS measurements were again performed 24 h after completion of the antineoplastic drugs dosing and 1 h after the last Compound A dose. During all recording sessions, animals were anesthetized with 2% isoflurane and placed in a prone position on a warm heating pad with rectal temperature monitored and maintained between 37.0-41.0° C. Stimulation of each nerve segment was performed at least 3 times, up to a maximum of 6 times, with increasing voltage, until the maximal response had been achieved. Latencies were scored from stimulus onset, and potential amplitudes from baseline.

DRG and Sciatic Nerve Morphology

At the end of the oxaliplatin and bortezomib experiments, animals were sacrificed under deep anaesthesia. SN segments and L5 and L6 DRG were dissected from 5 animals/group and embedded for analysis as previously described (31).

IENFD Analysis

IENFD analysis was performed on specimens collected and processed as previously described (31). Four sections were processed for each biopsy. Intra-epidermal unmyelinated axons were counted in a blinded fashion and the fiber density per mm of skin fibers that cross the dermal/epidermal junction was determined as previously described.

Statistical Analysis

For all statistical analysis, data were analyzed comparing mean group responses using one or two way ANOVA followed by Tukey's or Dunnet's post-hoc comparisons, made using Prism Graphpad software Version 4.03 (GraphPad Inc, La Jolla, California), with significance being defined at $p<0.05$.

RESULTS

Cisplatin Study

Food Intake and Body Weight Changes

Cisplatin treatment induced significant decrease in daily food intake and body weight ($p<0.05$, FIGS. 1A, 1B) compared to vehicle-treated rats. Compound A treatment at 3, 10 and 30 mg/kg increased overall food intake and body weight ($p<0.05$) compared to cisplatin alone.

Allodynia

Treatment with cisplatin decreased the paw withdrawal threshold in rats compared to vehicle-treated rats ($p<0.01$), indicating development of mechanical hypersensitivity. Pretreatment with Compound A at 10 and 30 mg/kg significantly reduced this hyperalgesia. Compound A treatment at 30 mg/kg actually resulted in overall significantly increased paw withdrawal thresholds compared to vehicle-treated rats ($p<0.05$) on Days 3 thru 5 (FIG. 1C). Compound A at 3 mg/kg had no significant effect on cisplatin-induced hyperalgesia.

Oxaliplatin Study

Body Weight Changes

Oxaliplatin-treated mice showed significant loss of body weight from Day 10 to the end of the study vs. vehicle-treated mice ($p<0.01$). The animals co-treated with oxaliplatin and 10 or 30 mg/kg Compound A showed less weight loss than the oxaliplatin treated mice ($p<0.01$). This effect reached statistical significance ($p<0.05$) on multiple test days, with 10 mg/kg Compound A having the most robust effect (data not shown).

Nerve Conduction Studies

Figure 2:
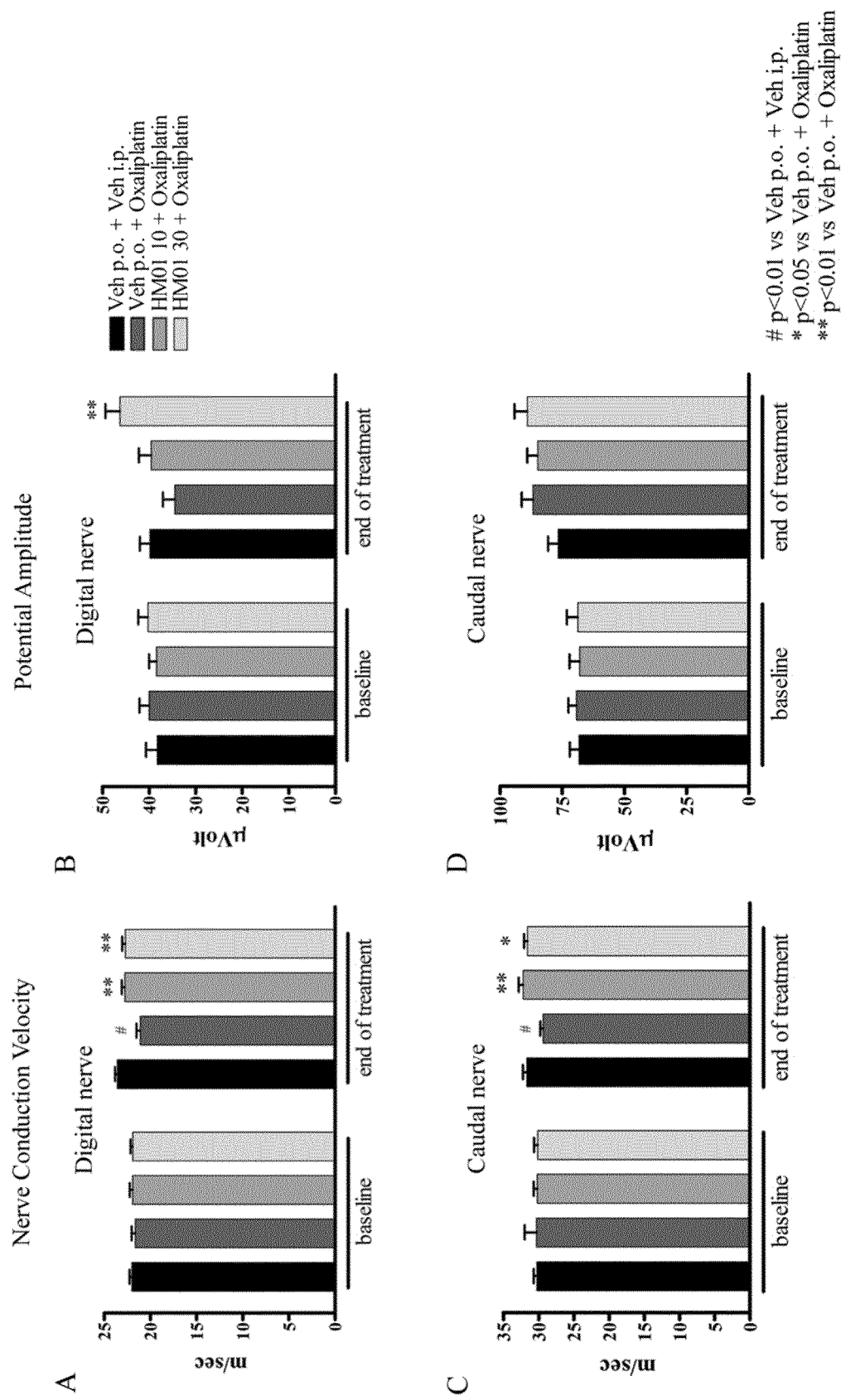
FIG. 2: Effect of Compound A on nerve conduction velocity (NCV) and potential amplitude in oxaliplatin-treated mice. All the parameters were measured prior to and 24 h after completion of dosing regimen consisting of vehicle or Compound A (10 or 30 mg/kg) PO daily, followed by oxaliplatin (6 mg/kg) or vehicle (every 4 days for a total 8 administrations) IP. Last Compound A dose was administered 1 h before recording. (* denotes $p=<0.05$ vs veh/oxaliplatin; #=$p<0.05$ vs veh/veh). A) and C) The administration of Compound A at 10 and 30 mg/kg significantly prevented the decrease in digital and caudal NCV observed in oxaliplatin-treated mice. B) Digital potential amplitude was decreased by oxaliplatin administration and the treatment with Compound A trended to normalize the potential amplitude, but only the administration of Compound A 30 mg/kg was able to normalize this data. D) Caudal nerve potential amplitude was not significantly affected by oxaliplatin treatment.

Oxaliplatin administration caused a significant decrease in digital and caudal NCV (reduced by 10.6±1.6% and 8±1.1% respectively, $p<0.01$) vs. vehicle-treated mice. Concurrent treatment with Compound A at both 10 and 30 mg/kg significantly prevented both these impairments (FIGS. 2A, 2C). Digital potential amplitude was also decreased by oxaliplatin (13.5+/−6.4%), although given the variability the effect did not reach statistical significance. Compound A treatment trended to normalize the potential amplitude decrease, so that at 30 mg/kg digital potential amplitude was significantly improved vs. oxaliplatin-treated mice (by 33+/−9%; p<0.01; FIG. 2B). Caudal nerve potential amplitude was not significantly affected by oxaliplatin treatment (FIG. 2D).

Pathological Examination

No degenerative changes in the DRG neuronal cell bodies or satellite cells or in the sciatic nerve from the oxaliplatin-treated mice were observed, and Compound A treatment itself did not cause any degenerative changes (data not shown).

Figure 3:
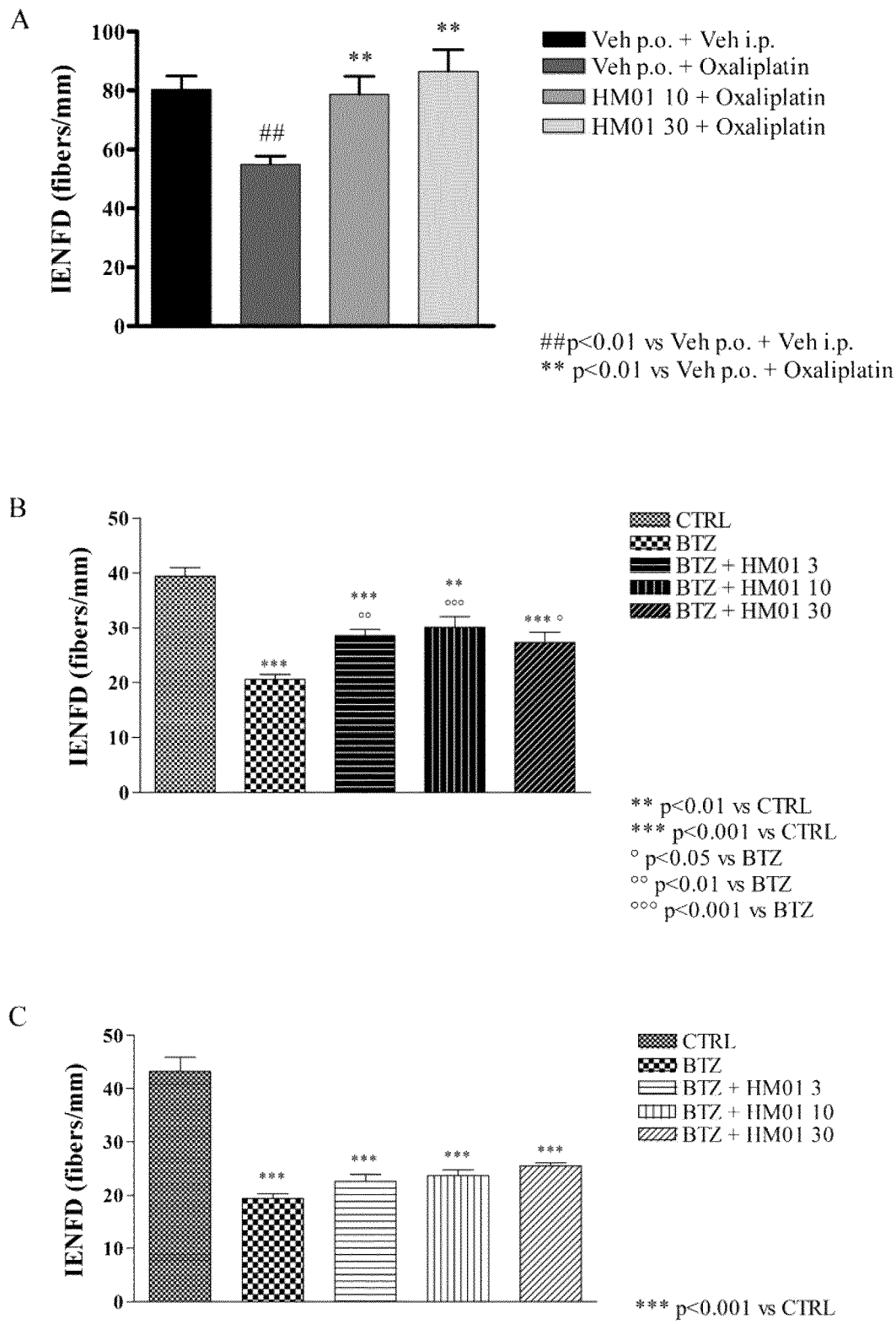
FIG. 3: Compound A reverted the reduction of intraepidermal nerve fiber density (IENFD). IENFD was measured 24 h after last Compound A dose. Oxaliplatin produced a significant decrease in fiber number which was completely normalised by treatment with COMPOUND A at 10 or 30 mg/kg daily ($p<0.01$). A) The administration of Compound A at both 10 and 30 mg/kg was able to normalize IENFD to vehicle treated mouse. B) and C) Chronic treatment with bortezomib induced a statistically significant reduction in IENFD; in the preventive setting, but not in the therapeutic setting, all doses of Compound A significantly prevented this reduction.

In the footpads, oxaliplatin treatment produced a significant reduction in IENFD (−31.7±3.5%, p<0.01 vs. vehicle-treated mice). Concurrent Compound A treatment completely normalized IENFD to vehicle treated mouse values at both 10 and 30 mg/kg (p<0.01; FIG. 3A).

Compound A Pharmacokinetics Following Acute and Chronic Administration

Figure 4:
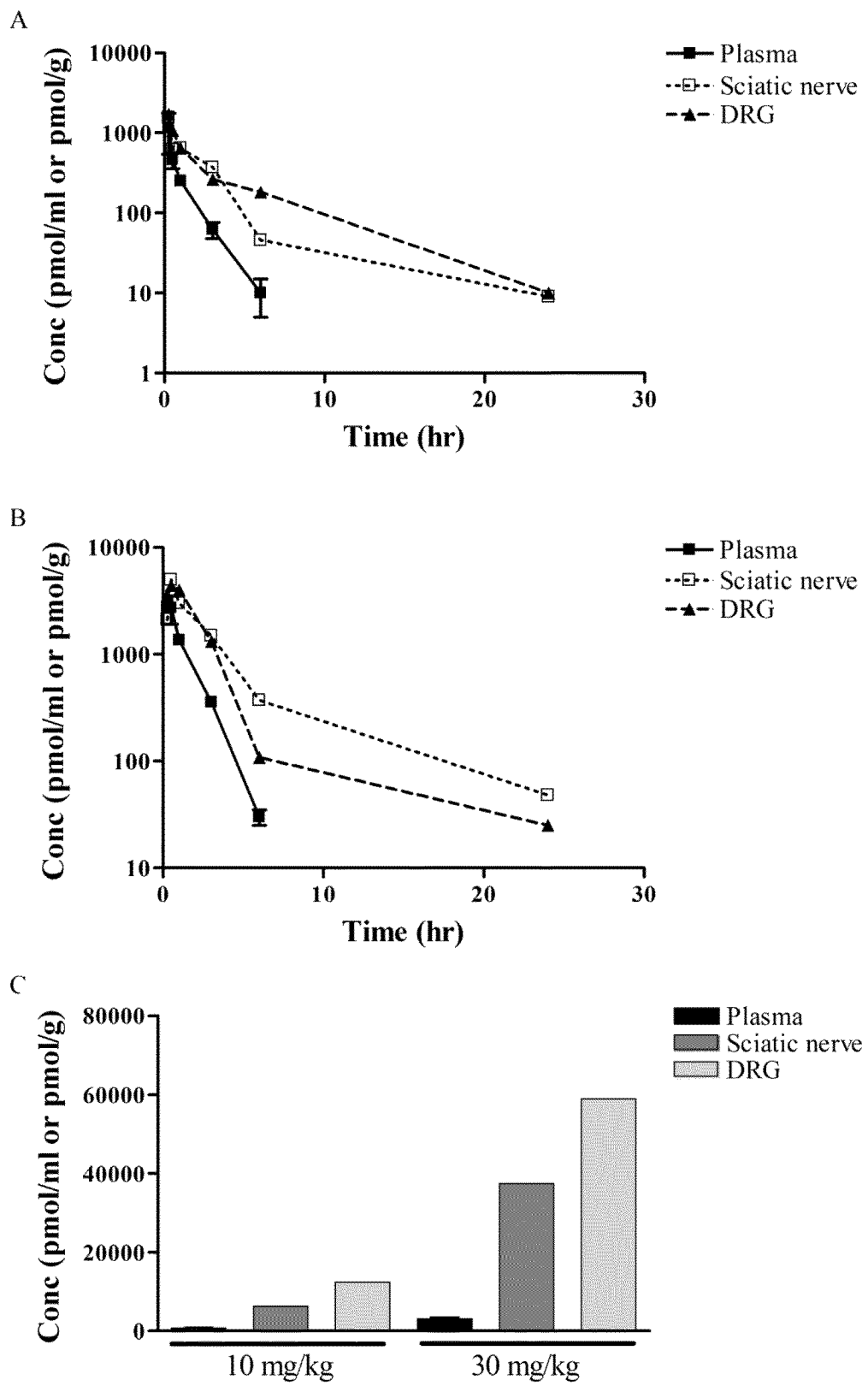
FIG. 4: Plasma, DRG and sciatic nerve concentrations of Compound A. A) and B) After a single oral dose of Compound A at both 10 and 30 mg/kg the compound was readily absorbed and distributed in plasma and nerve tissues with peak concentrations within 0.25-0.5 h. The terminal half-life was short in plasma, but significantly longer in sciatic nerve and DRG; the compound showed excellent tissue penetration into both the sciatic nerves and DRG. C) After 30 days of daily dosing, the concentration of Compound A was very low in plasma but elevated in sciatic nerve and DRG suggesting marked accumulation of Compound A in these tissues.

Compound A demonstrated very high and dose dependent sciatic nerve and DRG exposure. After a single oral dose of 10 and 30 mg/kg, Compound A was readily absorbed and distributed in plasma and nerve tissues with peak concentrations within 0.25-0.5 h post dose. The terminal half-life of Compound A in plasma was short (approximately 1 h), but significantly longer in sciatic nerve (approximately 4.7 h). The area under the concentration-time curve extrapolated to infinity ($AUC_{0-\infty}$) was lowest in plasma and almost 3-4 fold higher in sciatic nerve and DRG, and correlated with administered doses, suggesting enhanced penetration of Compound A into peripheral nervous system (Table 1, FIGS. 4A-B). After 30 days of daily dosing, the tissue penetration index (ratio of tissue/plasma) of Compound A was further enhanced to about 9-12 fold in SN and 18-19 fold in DRG suggesting marked accumulation of Compound A in these tissues (Table 1 and FIG. 4C).

Bortezomib Studies

Body Weight Changes

In the preventive study, during the first few weeks and until day 21 the animals co-treated with bortezomib and Compound A at different doses showed a significant increase in body weight vs. CTRL and bortezomib groups at several time points. This difference, however, was not significant at the end of treatment (data not shown).

In the therapeutic setting, following 10 days co-treatment of bortezomib with Compound A, animals showed a significant increase of body weight vs. CTRL and bortezomib groups. At the end of treatment only the animals treated with BTZ+Compound A 30 showed a significant increase in body weight vs. CTRL and bortezomib groups (p<0.01, data not shown).

Mechanical Threshold

Figure 5:
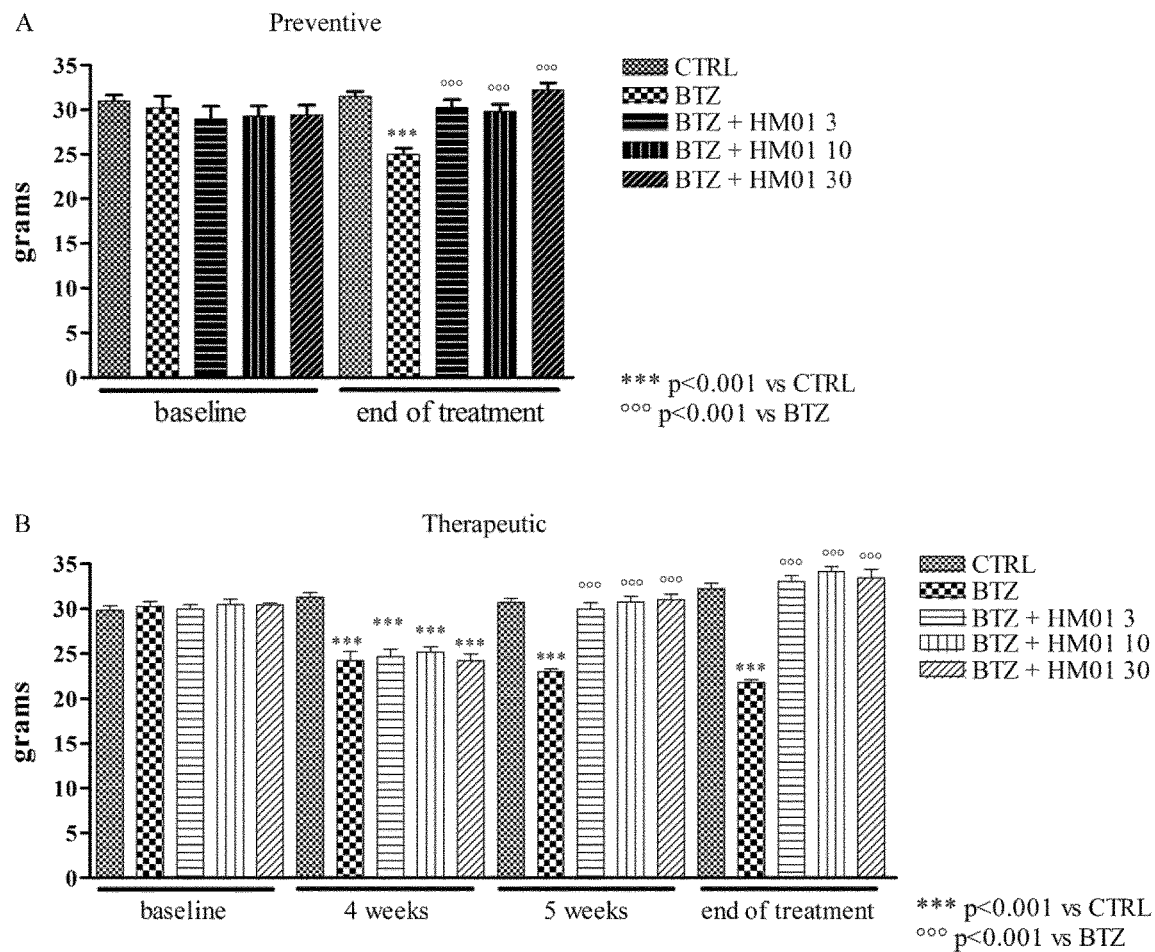
FIG. 5: Compound A administration reverted the allodynia induced by bortezomib. Preventive setting. A) At the end of treatment the groups treated with bortezomib in combination with all doses of Compound A did not show allodynia, while this was observed in the rats treated with bortezomib alone. Therapeutic setting. B) Before the beginning of co-administration with Compound A (4 weeks) all bortezomib-treated animals developed allodynia. After one week from the start of the co-treatment and at the end of treatment, only the groups treated with bortezomib alone had allodynia, while all the groups co-treated with Compound A were protected.

In both the bortezomib studies, mechanical threshold was reduced by antineoplastic drug administration. At the end of treatment in the preventive setting the groups treated with bortezomib in combination with Compound A did not show allodynia vs CTRL, while this was observed in the bortezomib group (p<0.001, FIG. 5A).

In the therapeutic setting (FIG. 5B), after 4 weeks all groups treated with bortezomib showed the development of allodynia with a reduction in the latency until withdrawal vs CTRL (p<0.001 vs CTRL). After 5 weeks (i.e. 1 week of co-treatment BTZ+Compound A) and at the end of treatment, only the groups treated with bortezomib alone had allodynia vs CTRL, while all the groups co-treated with Compound A were protected (p<0.001).

Nerve Conduction Studies

Figure 6:
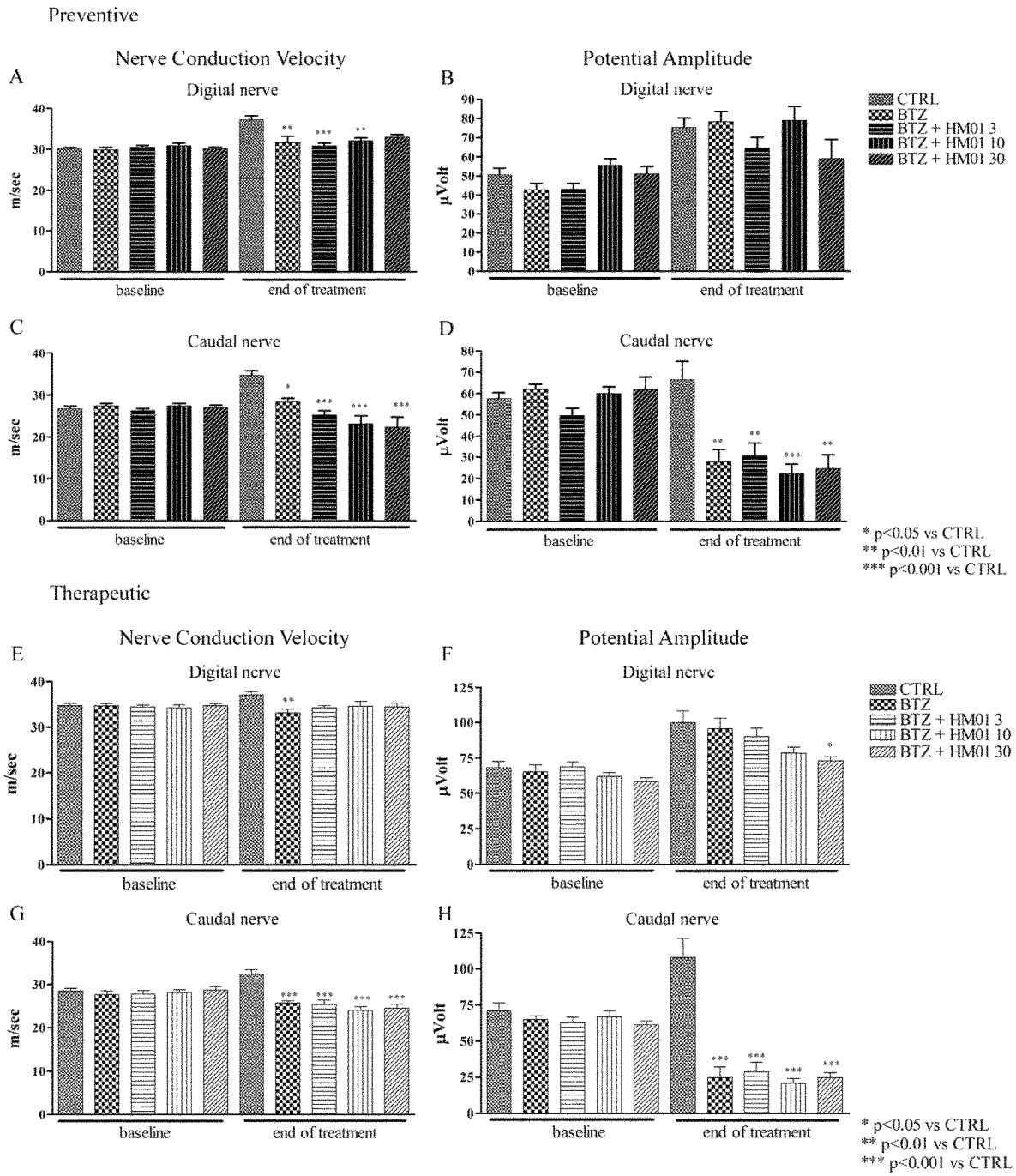
FIG. 6: Effect of Compound A on nerve conduction velocity (NCV) and potential amplitude in bortezomib-treated rats. Preventive setting. A) The treatment with bortezomib alone or in combination with Compound A at the doses of 3 and 10 mg/kg showed a statistically significant reduction in digital NCV, while the group co-treated with the highest dose of Compound A had no alteration if compared to CTRL. B) No changes in digital potential amplitude were observed in all groups. C) and D) All groups treated with bortezomib alone or in combination with all doses of Compound A showed a significant reduction in caudal NCV and potential amplitude. Therapeutic setting. E) and F) Only the animals treated with bortezomib alone showed a significant reduction in digital NCV, while a reduction in potential amplitude was observed only in the group co-treated with the highest dose of Compound A. G) and H) As shown in preventive setting, all groups treated with bortezomib alone or in combination with all doses of Compound A had a significant reduction in caudal NCV and potential amplitude.

In digital NCV the groups treated with bortezomib alone or in combination with Compound A 3 and 10 mg/kg in the preventive setting showed a statistically significant reduction (p<0.01 vs CTRL), while the group co-treated with BTZ+Compound A 30 mg/kg had no alteration vs. CTRL (FIG. 6A). No changes in digital potential amplitude were observed in all groups vs CTRL at the end of treatment (FIG. 6B).

All groups treated with bortezomib alone or in combination with all doses of Compound A in the preventive setting showed a statistically significant reduction in caudal NCV (p<0.05) as well as in caudal potential amplitude (p<0.01 vs CTRL, FIGS. 6C, 6D).

In the therapeutic setting, digital nerve NCV showed a statistically significant reduction only the animals treated with bortezomib alone (p<0.05 vs CTRL, FIG. 6E), while a reduction in potential amplitude was observed in the group co-treated with the highest dose of Compound A (p<0.05 vs CRTL, FIG. 6F). All groups treated with bortezomib alone or in combination with all doses of Compound A showed a statistically significant reduction in caudal NCV and potential amplitude (p<0.001 vs CTRL, FIGS. 6G, 6H).

Pathological Examination

Bortezomib-treated mice showed occasional degeneration of DRG sensory neurons and vacuolization of cytoplasm of satellite cells. The co-administration of Compound A in the preventive setting produced incomplete protection from these alterations. In the sciatic nerve mild axonal changes were evident in all the bortezomib-treated groups, and the co-administration of Compound A at different doses did not alter these changes.

In the caudal nerve the animals treated with bortezomib alone had reduced fiber density, axonal and Schwann cells degeneration and the animals co-treated with bortezomib and Compound A at different doses showed a mild, not dose-dependent reduction in these pathological changes.

These protective effects were not present when Compound A was delivered in the therapeutic setting.

Chronic treatment with bortezomib induced a statistically significant reduction in IENFD if compared vs. CTRL (p<0.001). All doses of Compound A significantly prevented the reduction in IENFD induced by bortezomib in the preventive (FIG. 3B), but not in the therapeutic setting (FIG. 3C), although an inhibitory trend was observed.

Proteasome Inhibition Study

Chronic treatment with bortezomib induced a statistically significant inhibition of proteasome activity; the co-administration of Compound A at different doses did not impair bortezomib-induced proteasome inhibition either in preventive or therapeutic settings (data not shown).

A summary of the assessment results in multiple neurotoxicity models is presented in the following table:

| Drug and schedule | Compound A dose | Body Weight | Allodynia | NCS | IENFD | DRG/nerve pathology |
|---|---|---|---|---|---|---|
| Cisplatin | 3 | + | ND | ND | ND | ND |
| 0.5 mg/kg (i.p.) | 10 | + | + | ND | ND | ND |
| for three days | 30 | + | + | ND | ND | ND |
| Oxaliplatin | 10 | + | ND | + | + | = |
| 6 mg/kg (i.p.) twice weekly for 4 weeks | 30 | + | ND | + | + | = |
| Bortezomib | 3 | +/− | + | − | + | − |
| Preventive setting | 10 | +/− | + | − | + | +/− |
| 0.2 mg/kg (i.v.) 3 times/week for 8 weeks | 30 | +/− | + | +/− | + | +/− |
| Bortezomib | 3 | +/− | + | +/− | − | − |
| Therapeutic setting | 10 | +/− | + | +/− | − | +/− |
| 0.2 mg/kg (i.v.) 3 times/week for 8 weeks | 30 | +/− | + | − | − | +/− |

+ significant effect of Compound A vs. antineoplastic drug;
+/− partial effect of Compound A vs. antineoplastic drug;
− no effect of Compound A vs. antineoplastic drug;
= no effect of theantineoplastic drug

Discussion

Using well-accepted acute and chronic preclinical CIPN models, we tested the effect of Compound A administration. Moreover, in the bortezomib models we also verified that no interference with the antineoplastic mechanism of action of the drug occurred. These animal models have been extensively used to test the effectiveness of putative neuroprotective treatments, thus providing the rationale for their use in our study.

In all the tested conditions we consistently observed reduction in mechanical allodynia. These results are particularly important in bortezomib models, since this is the antineoplastic drug that induces the most painful, dose-limiting CIPN. The anti-nociceptive effects observed in our study is very rapid, as demonstrated by the results of the cisplatin study, and it might be centrally mediated since Compound A is highly brain penetrable.

However, the results obtained using long-term administration suggest that Compound A also has some trophic peripheral effect, since it provides a significant protection from drug-induced reduction in IENFD in both oxaliplatin and bortezomib models. Remarkably, in the therapeutic setting reduction in allodynia was still significant, but it was not associated with any effect on IENFD, thus further supporting the hypothesis of a central analgesic effect that is dissociated from the peripheral neuroprotection and that the latter can occur only if Compound A treatment is started before small fiber depletion.

Besides this effect, Compound A additional activity on myelinated fibers of the peripheral branch of the nervous system sensory neuron is supported by the demonstration that Compound A attenuates some of the neurophysiologic deficits induced by chronic multiple dosing of oxaliplatin and, to a lesser extent, of bortezomib. In fact, this neurophysiologically evident effect directly measured in peripheral nerves and reflecting mainly the activity of large myelinated fibers cannot be attributed to a central event, while rather, it is likely to be due to preservation in the responding number of peripheral axons.

The presence of a bell shaped dose-response to Compound A, where 10 mg/kg was also observed.

The marked capacity of Compound A to penetrate in the CNS, coupled with its peripheral neurotrophic activity, its non drug-specific activity and its possible use to treat cancer cachexia makes Compound A a unique putative neuroprotective agent in cancer patients undergoing a neurotoxicity-inducing chemotherapy.

Example 7

Cardiovascular Effects of Compound A in Human Volunteers (Phase 1 Study)

The study was performed as a single-center, randomized, double-blind, placebo-controlled, Phase 1 study with healthy male subjects receiving single ascending oral doses of Compound A. A dose-escalation design was considered to be appropriate to investigate the safety and tolerability of this new compound in the first single dose study in humans. Within each cohort six subjects were to receive a single oral dose of Compound A and two subjects were to receive placebo on Day 1.

| |
|---|
| Cohort 1: 10 mg Compound A |
| Cohort 2: 0.1 mg Compound A |
| Cohort 3: 0.3 mg Compound A |
| Cohort 4: 1.0 mg Compound A |

Each subject received a single oral dose of either Compound A or placebo in a randomized fashion. Study drug administrations were performed in the morning of Day 1. The proper administration of the study medication was supervised by the Investigator or delegate. This included checking the oral and buccal cavity. The study medication or placebo was supplied as powder-containing gelatin capsules; they were administered orally together with 240 mL water. Subjects were dosed in a fasted state (no food was taken for at least 8 hours prior to dosing). Access to food was restricted until 4 hours after dosing.

12-lead ECGs were recorded on Day −1 and from pre-dose on Day 1 to 72 hours after drug administration. In addition, a Holter-ECG was recorded from about at least 12 hours prior to the planned dosing until 24 hours post-dose. Triplicate extracts (1 min interval) were taken at the same time-points when paper ECGs were taken. Vital signs (blood pressure, pulse rate, body temperature [auricular measurement]) were measured on Day −1 and then from pre-dose on Day 1 to 72 hours post-dose. 12-lead ECGs were recorded as scheduled in the study flow chart using the ECG system (Cardiosoft, Marquette Hellige). Triplicate ECGs were recorded at 36, 48 and 72 hours post-dose. The ECGs were recorded in supine position after at least 5 minutes rest or after at least 15 minutes rest at time points when ECG extracts from the Holter-ECG were done (to allow for a sufficient time period). ECGs were plotted with a paper speed of 50 mm/s and 10 mm/mV amplitude, with 10 seconds recording duration for all leads and at least 3 complexes, but preferably 5 complexes in each lead. The following ECG parameters were evaluated: heart rate, PR interval, QRS interval, QT interval, QTcB (using Bazett's correction formula) and QTcF (using Fridericia's correction formula).

Mean systolic and diastolic blood pressure and body temperature showed no clinically relevant changes after dosing or differences between the treatment groups. A decrease in pulse rate was observed for the groups treated with Compound A.

Figure 7:
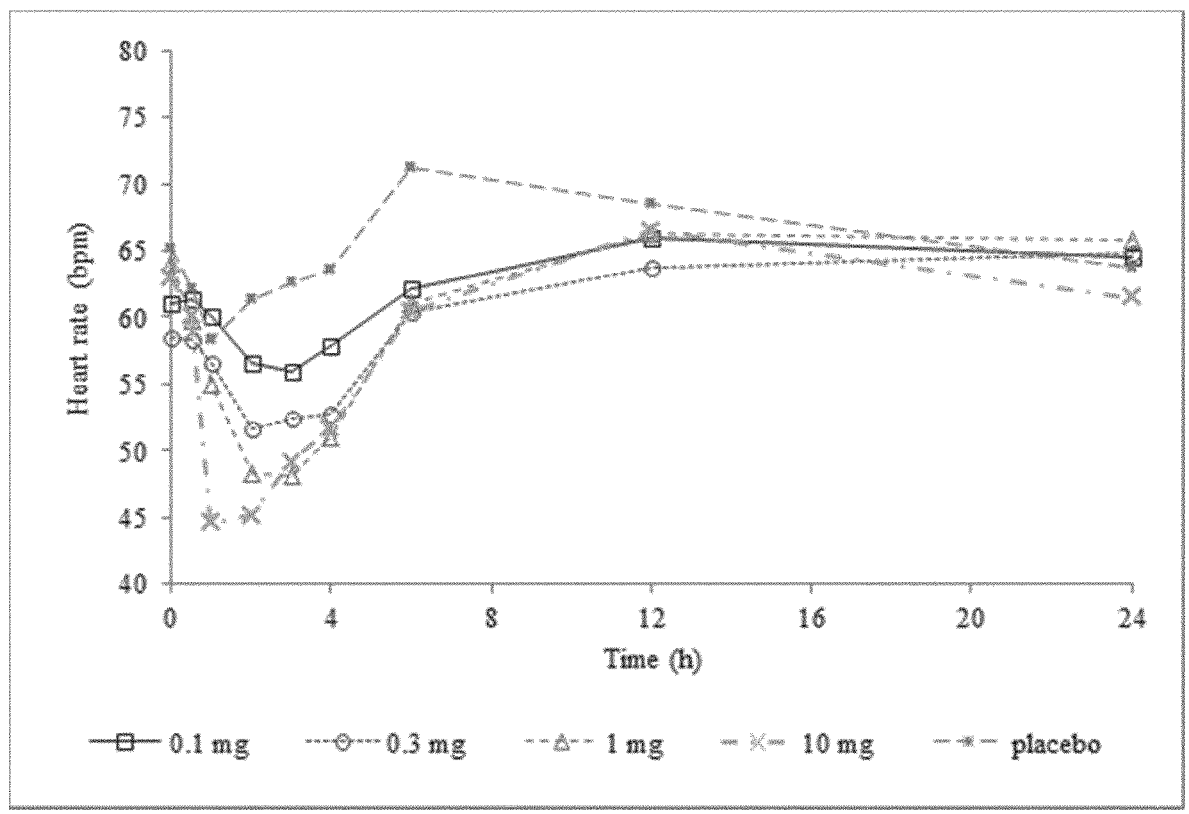
FIG. 7: mean heart rate—absolute values (mean from the average of triplicate readings) of human patients treated with doses of 0.1, 0.3, 1 or 10 mg of Compound A, compared to placebo.
Figure 8:
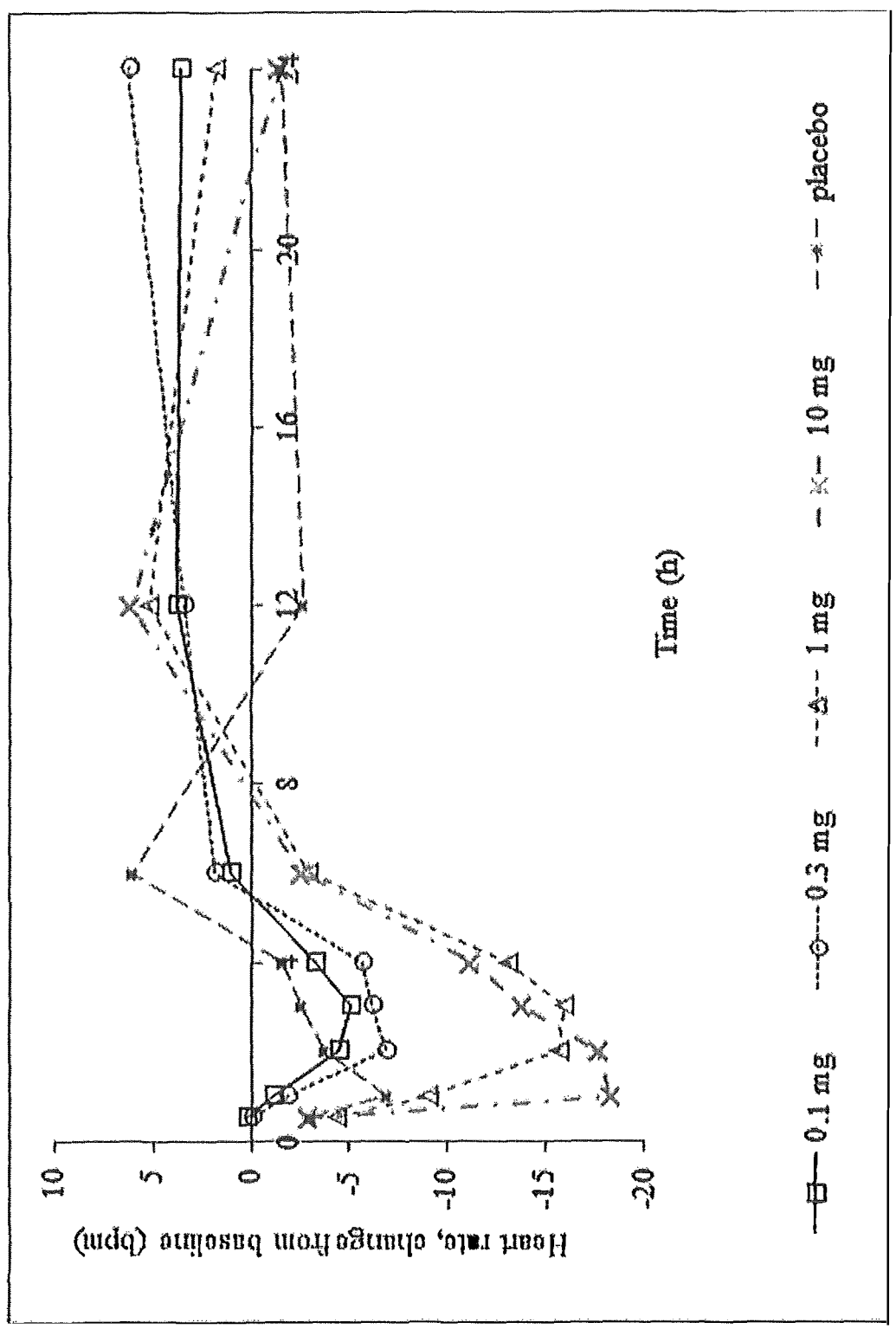
FIG. 8: mean heart rate—changes from baseline (mean from the average of triplicate readings) of human patients treated with doses of 0.1, 1, 0.3 or 10 mg of Compound A, compared to placebo.

FIGS. 7 and 8 show the results obtained. They show a clear dose-related decrease in heart rate, which reached a maximum at 1 to 3 hours after dosing. Mean heart rate (Holter-ECG data, mean from the average of triplicate readings) decreased by maximally 5.1 bpm, 6.8 bpm, 15.9 bpm and 18.3 bpm at 1 to 3 hours after administration of 0.1, 0.3, 1.0 and 10 mg Compound A, respectively, compared to a maximum decrease of 6.9 bpm after placebo dosing. Pre-dose levels were reached again 6 hours after dosing. The lowest heart rate values were observed in the 1.0 and 10 mg dose groups.

REFERENCES

1. Howard A D, Feighner S D, Cully D F, Arena J P, Liberator P A, Rosenblum C I, et al. A receptor in pituitary and hypothalamus that functions in growth hormone release. *Science* 1996; 273:974-7
2. Kojima M, Hosoda H, Date Y, Nakazato M, Matsuo H, Kangawa K. Ghrelin is a growth-hormone-releasing acylated peptide from stomach. *Nature* 1999; 402:656-60
3. Nakazato M, Murakami N, Date Y, Kojima M, Matsuo H, Kangawa K, et al. A role for ghrelin in the central regulation of feeding. *Nature* 2001; 409:194-8
4. Tschop M, Smiley D L, Heiman M L. Ghrelin induces adiposity in rodents. *Nature* 2000; 407:908-13
5. Hotta M, Ohwada R, Akamizu T, Shibasaki T, Takano K, Kangawa K. Ghrelin increases hunger and food intake in patients with restricting-type anorexia nervosa: a pilot study. *Endocr J* 2009; 56:1119-28
6. Temel J S, Abernethy A P, Currow D C, Friend J, Duus E M, Yan Y, et al. Anamorelin in patients with non-small-cell lung cancer and cachexia (ROMANA 1 and ROMANA 2): results from two randomised, double-blind, phase 3 trials. *Lancet Oncol* 2016; 17:519-31
7. Collden G, Tschop M H, Muller T D. Therapeutic Potential of Targeting the Ghrelin Pathway. *Int J Mol Sci* 2017; 18
8. Kluge M, Schussler P, Dresler M, Schmidt D, Yassouridis A, Uhr M, et al. Effects of ghrelin on psychopathology, sleep and secretion of cortisol and growth hormone in patients with major depression. *J Psychiatr Res* 2011; 45:421-6
9. Nagaya N, Moriya J, Yasumura Y, Uematsu M, Ono F, Shimizu W, et al. Effects of ghrelin administration on left ventricular function, exercise capacity, and muscle wasting in patients with chronic heart failure. *Circulation* 2004; 110:3674-9
10. Sanger G J, Furness J B. Ghrelin and motilin receptors as drug targets for gastrointestinal disorders. *Nat Rev Gastroenterol Hepatol* 2016; 13:38-48
11. Steculorum S M, Bouret S G. Developmental effects of ghrelin. *Peptides* 2011; 32:2362-6
12. Chung H, Kim E, Lee D H, Seo S, Ju S, Lee D, et al. Ghrelin inhibits apoptosis in hypothalamic neuronal cells during oxygen-glucose deprivation. *Endocrinology* 2007; 148:148-59
13. Furness J B, Hunne B, Matsuda N, Yin L, Russo D, Kato I, et al. Investigation of the presence of ghrelin in the central nervous system of the rat and mouse. *Neuroscience* 2011; 193:1-9
14. Ferrini F, Salio C, Lossi L, Merighi A. Ghrelin in central neurons. *Curr Neuropharmacol* 2009; 7:37-49
15. Theil M M, Miyake S, Mizuno M, Tomi C, Croxford J L, Hosoda H, et al. Suppression of experimental autoimmune encephalomyelitis by ghrelin. *J Immunol* 2009; 183:2859-66
16. Moon M, Kim H G, Hwang L, Seo J H, Kim S, Hwang S, et al. Neuroprotective effect of ghrelin in the 1-methyl-4-phenyl-1,2,3,6-tetrahydropyridine mouse model of Parkinson's disease by blocking microglial activation. *Neurotox Res* 2009; 15:332-47
17. Gahete M D, Cordoba-Chacon J, Kineman R D, Luque R M, Castano J P. Role of ghrelin system in neuroprotection and cognitive functions: implications in Alzheimer's disease. *Peptides* 2011; 32:2225-8
18. Raimondo S, Ronchi G, Geuna S, Pascal D, Reano S, Filigheddu N, et al. Ghrelin: a novel neuromuscular recovery promoting factor? *Int Rev Neurobiol* 2013; 108:207-21
19. Baatar D, Patel K, Taub D D. The effects of ghrelin on inflammation and the immune system. *Mol Cell Endocrinol* 2011; 340:44-58
20. Tsuchimochi W, Kyoraku I, Yamaguchi H, Toshinai K, Shiomi K, Kangawa K, et al. Ghrelin prevents the development of experimental diabetic neuropathy in rodents. *Eur J Pharmacol* 2013; 702:187-93
21. Zhou C H, Li X, Zhu Y Z, Huang H, Li J, Liu L, et al. Ghrelin alleviates neuropathic pain through GHSR-1a-mediated suppression of the p38 MAPK/NF-kappaB pathway in a rat chronic constriction injury model. *Reg Anesth Pain Med* 2014; 39:137-48
22. Garcia J M, Cata J P, Dougherty P M, Smith R G. Ghrelin prevents cisplatin-induced mechanical hyperalgesia and cachexia. *Endocrinology* 2008; 149:455-60
23. Wei J, Zhi X, Wang X L, Zeng P, Zou T, Yang B, et al. In vivo characterization of the effects of ghrelin on the modulation of acute pain at the supraspinal level in mice. *Peptides* 2013; 43:76-82
24. Granado M, Priego T, Martin A I, Villanua M A, Lopez-Calderon A. Anti-inflammatory effect of the ghrelin agonist growth hormone-releasing peptide-2 (GHRP-2) in arthritic rats. *Am J Physiol Endocrinol Metab* 2005; 288:E486-92
25. Banks W A, Tschop M, Robinson S M, Heiman M L. Extent and direction of ghrelin transport across the blood-brain barrier is determined by its unique primary structure. *J Pharmacol Exp Ther* 2002; 302:822-7
26. Hosoda H, Kangawa K. Standard sample collections for blood ghrelin measurements. *Methods Enzymol* 2012; 514:113-26

27. Tong J, Dave N, Mugundu G M, Davis H W, Gaylinn B D, Thorner M O, et al. The pharmacokinetics of acyl, des-acyl, and total ghrelin in healthy human subjects. *Eur J Endocrinol* 2013; 168:821-8

28. Chaplan S R, Bach F W, Pogrel J W, Chung J M, Yaksh T L. Quantitative assessment of tactile allodynia in the rat paw. *J Neurosci Methods* 1994; 53:55-63

29. Wozniak K M, Nomoto K, Lapidus R G, Wu Y, Carozzi V, Cavaletti G, et al. Comparison of neuropathy-inducing effects of eribulin mesylate, paclitaxel, and ixabepilone in mice. *Cancer Res* 2011; 71:3952-62

30. Meregalli C, Canta A, Carozzi V A, Chiorazzi A, Oggioni N, Gilardini A, et al. Bortezomib-induced painful neuropathy in rats: a behavioral, neurophysiological and pathological study in rats. *Eur J Pain* 2010; 14:343-50

31. Carozzi V A, Canta A, Oggioni N, Sala B, Chiorazzi A, Meregalli C, et al. Neurophysiological and neuropathological characterization of new murine models of chemotherapy-induced chronic peripheral neuropathies. *Experimental Neurology* 2010; 226:301-9

32. Kaplan G S, Torcun C C, Grune T, Ozer N K, Karademir B. Proteasome inhibitors in cancer therapy: Treatment regimen and peripheral neuropathy as a side effect. *Free Radic Biol Med* 2017; 103:1-13

The invention claimed is:

1. A method of treating a medical condition mediated by the ghrelin receptor in the central nervous system of a subject in need thereof, the method comprising administering compound 3-(1-(2,3-dichloro-4-methoxyphenyl)ethyl)-1-methyl-1-(1,3,3-trimethylpiperidin-4-yl)urea monohydrochloride salt to the subject.

2. The method of claim 1, wherein said medical condition is neurodegeneration, neuropathy, neuropathic pain, encephalomyelitis, Parkinson's Disease, Alzheimer's Disease, cognitive disorders, vagal hyperstimulation, or tachycardia.

3. The method of claim 2, wherein said neuropathy is a chemotherapy-induced neuropathy.

4. The method of claim 3, wherein said chemotherapy-induced neuropathy is induced by a proteasome inhibitor or an alkylating agent.

5. The method of claim 4, wherein said proteasome inhibitor is bortezomib, carfilzomib, ixazomib, oprozomib, delanzomib, marizomib, MG-132, ONX-0914, VR-23, celastrol, or epoxomicin.

6. The method of claim 4, wherein said alkylating agent is cisplatin or carboplatin.

7. The method of claim 2, wherein said tachycardia is a chemotherapy-induced tachycardia.

8. The method of claim 1, wherein said compound is administered in a dose amount ranging from about 0.03 and to about 10 mg, expressed as free base.

9. The method of claim 1, wherein said compound is administered externally to the central nervous system.

10. The method of claim 9, wherein said compound is administered by an oral, peroral, buccal, sublingual, ocular, percutaneous, transcutaneous, intravenous, intramuscular, inhalatory or rectal route.

11. The method of claim 3, wherein said compound is administered in a dose amount ranging from about 0.03 to about 10 mg, expressed as free base.

12. The method of claim 4, wherein said compound is administered in a dose amount ranging from about 0.03 to about 10 mg, expressed as free base.

13. The method of claim 7, wherein said compound is administered in a dose amount ranging from about 0.03 to about 10 mg, expressed as free base.

14. The method of claim 3, wherein said compound is administered externally to the central nervous system.

15. The method of claim 4, wherein said compound is administered externally to the central nervous system.

16. The method of claim 7, wherein said compound is administered externally to the central nervous system.

17. A method of preventing a medical condition mediated by the ghrelin receptor in the central nervous system of a subject in need thereof, the method comprising administering compound 3-(1-(2,3-dichloro-4-methoxyphenyl)ethyl)-1-methyl-1-(1,3,3-trimethylpiperidin-4-yl)urea monohydrochloride salt to the subject, wherein the medical condition is chemotherapy-induced neuropathy.

18. The method of claim 17, wherein said chemotherapy-induced neuropathy is induced by a proteasome inhibitor or an alkylating agent.

19. The method of claim 18, wherein said proteasome inhibitor is bortezomib, carfilzomib, ixazomib, oprozomib, delanzomib, marizomib, MG-132, ONX-0914, VR-23, celastrol, or epoxomicin.

20. The method of claim 18, wherein said alkylating agent is cisplatin or carboplatin.

21. The method of claim 17, wherein said compound is administered in a dose amount ranging from about 0.03 to about 10 mg, expressed as free base.

22. The method of claim 17, wherein said compound is administered externally to the central nervous system.

* * * * *

UNITED STATES PATENT AND TRADEMARK OFFICE
CERTIFICATE OF CORRECTION

| | | |
|---|---|---|
| PATENT NO. | : 12,005,056 B2 | Page 1 of 1 |
| APPLICATION NO. | : 16/982107 | |
| DATED | : June 11, 2024 | |
| INVENTOR(S) | : Giuliano et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this
Eighth Day of October, 2024

Katherine Kelly Vidal
*Director of the United States Patent and Trademark Office*